US010220117B2

(12) United States Patent
Zhang et al.

(10) Patent No.: US 10,220,117 B2
(45) Date of Patent: Mar. 5, 2019

(54) METHODS OF MAMMALIAN RETINAL STEM CELL PRODUCTION AND APPLICATIONS

(71) Applicant: The Regents of the University of California, Oakland, CA (US)

(72) Inventors: Kang Zhang, San Diego, CA (US); Jiagang Zhao, San Diego, CA (US); Adah Almutairi, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 63 days.

(21) Appl. No.: 15/028,618

(22) PCT Filed: Oct. 9, 2014

(86) PCT No.: PCT/US2014/059951
§ 371 (c)(1),
(2) Date: Apr. 11, 2016

(87) PCT Pub. No.: WO2015/054526
PCT Pub. Date: Apr. 16, 2015

(65) Prior Publication Data
US 2016/0243285 A1    Aug. 25, 2016

Related U.S. Application Data

(60) Provisional application No. 61/888,846, filed on Oct. 9, 2013.

(51) Int. Cl.
*C12N 5/00*    (2006.01)
*C12N 5/02*    (2006.01)
*A61L 27/38*    (2006.01)
*C12N 5/0797*    (2010.01)
*A61K 35/30*    (2015.01)
*C12N 5/0793*    (2010.01)
*C12N 5/079*    (2010.01)
*A61L 27/52*    (2006.01)
*A61K 35/545*    (2015.01)
*A61L 27/24*    (2006.01)
*A61L 27/26*    (2006.01)
*A61L 27/54*    (2006.01)
*A61K 9/00*    (2006.01)

(52) U.S. Cl.
CPC ........ *A61L 27/3834* (2013.01); *A61K 9/0046* (2013.01); *A61K 35/30* (2013.01); *A61K 35/545* (2013.01); *A61L 27/24* (2013.01); *A61L 27/26* (2013.01); *A61L 27/3804* (2013.01); *A61L 27/3839* (2013.01); *A61L 27/52* (2013.01); *A61L 27/54* (2013.01); *C12N 5/062* (2013.01); *C12N 5/0621* (2013.01); *C12N 5/0623* (2013.01); *A61L 2300/64* (2013.01); *A61L 2430/16* (2013.01); *C12N 2500/33* (2013.01); *C12N 2500/38* (2013.01); *C12N 2500/90* (2013.01); *C12N 2501/115* (2013.01); *C12N 2501/15* (2013.01); *C12N 2501/155* (2013.01); *C12N 2501/16* (2013.01); *C12N 2501/165* (2013.01); *C12N 2501/39* (2013.01); *C12N 2501/395* (2013.01); *C12N 2501/415* (2013.01); *C12N 2501/42* (2013.01); *C12N 2501/727* (2013.01); *C12N 2501/999* (2013.01); *C12N 2506/02* (2013.01)

(58) Field of Classification Search
CPC .......................... A61L 27/3834; A61K 9/0046
See application file for complete search history.

(56) References Cited

U.S. PATENT DOCUMENTS

| | | |
|---|---|---|
| 2004/0224887 A1 | 11/2004 | Jessell et al. |
| 2007/0196919 A1 | 8/2007 | Reh et al. |
| 2008/0089868 A1 | 4/2008 | Zuber et al. |
| 2010/0105137 A1 | 4/2010 | Takahashi et al. |
| 2010/0105193 A1 | 4/2010 | Takahashi et al. |
| 2012/0142093 A1 | 6/2012 | Takahashi et al. |
| 2017/0130199 A1* | 5/2017 | Chambers ............ C12N 5/0619 |

FOREIGN PATENT DOCUMENTS

| | | |
|---|---|---|
| JP | 2013-128475 A | 7/2013 |
| WO | 2008/87917 A1 | 7/2008 |
| WO | 2012158910 A2 | 11/2012 |
| WO | 2013123292 A1 | 8/2013 |

OTHER PUBLICATIONS

Osakada (2009, Journal of Cell Science, 122:3169-3179).*
OsakadaB (2009, Nature Protocols, 4:811-824).*
Eiraku (2011, Nature, 472:51-56).*
Li (2009, Chinese Science Bulletin, 54:4214-4220).*
Chi (2016, Stem Cell Reports, 7:941-954).*
Matsuoka (2017, Stem Cells Translational Medicine, 6:923-936).*
Lovatt (2017, Differentiation, in press, attached as pp. 1-8).*
Greif, Gabriela, Partial Supplementary European Search Report, European Patent Office, Application No. 14852550.4, dated May 30, 2017.

(Continued)

*Primary Examiner* — Valarie E Bertoglio
(74) *Attorney, Agent, or Firm* — Joseph R. Baker, Jr.; Gavrilovich, Dodd & Lindsey LLP

(57) ABSTRACT

The invention provides an in vitro method for producing isolated mammalian primitive retinal stem cells (pRSCs) comprising: (a) culturing isolated embryonic stem cells (ESCs) from a mammal in a cell culture medium that is free of feeder cells, feeder-conditioned medium or serum so as to produce and grow a culture of the isolated ESCs; and (b) contacting the culture of the isolated ESCs so grown with one or more of an inhibitor for Wnt or TGF-β/BMP signaling so as to differentiate the isolated ESCs of (a) into primitive retinal stem cells thereby producing isolated mammalian pRSCs.

21 Claims, 8 Drawing Sheets
Specification includes a Sequence Listing.

(56) References Cited

OTHER PUBLICATIONS

Murry et al., "Differentiation of embryonic stem cells to clinically relevant populations: lessons from embryonic development", Cell, vol. 132(4), Feb. 1, 2008, pp. 661-680.
Nakamura, Yukari, International Preliminary Report on Patentability and Written Opinion, The International Bureau of WIPO, PCT/2014/059951, dated Apr. 21, 2016.
Cui et al., "WNT signaling determines tumorigenicity and function of ESC-derived retinal progenitors," J. Clin Invest., vol. 123, No. 4, pp. 1647-1661, Apr. 1, 2013.
Inman et al., "SB-431542 is a potent and specific inhibitor of transforming growth factor-beta superfamily type I activin receptor-like kinase (ALK) receptors ALK4, ALK5, and ALK7," Mol. Pharmacol., vol. 62, No. 1, pp. 65-74, Jul. 2002.
Ten Berge et al., "Embryonic stem cells require Wnt proteins to prevent differentiation to epiblast stem cells," Nat Cell Biol., vol. 13, No. 9, pp. 1070-1075, Aug. 14, 2011.
Young, Lee W., International Search Report, United States Patent & Trademakr Office, PCT/2014/059951, dated Mar. 26, 2015.
Cui et al., "WNT signaling determines tumorigenicity and function of ESC-derived retinal progenitors," J. Clin Invest., vol. 123, No. 4, pp. 1647-1661, epublished Mar. 25, 2013.
Greif, Gabriela, Extended European Search Report, European Patent Office, Application No. 14852550A, dated Sep. 7, 2017.
Office Action, Application No. 2016-521740, Japanese Patent Office, dated Jul. 23, 2018.
Yang, Li et al., "Maintenance of human embryonic stem cells on gelatin", Chinese Science Bulletin, Nov. 2009, vol. 54, No. 22, pp. 4215-4220.

\* cited by examiner

US 10,220,117 B2

METHODS OF MAMMALIAN RETINAL STEM CELL PRODUCTION AND APPLICATIONS

CROSS REFERENCE TO RELATED APPLICATIONS

This application is a U.S. National Phase application filed under 35 U.S.C. § 371 and claims priority to International Application No. PCT/US14/59951, filed on Oct. 9, 2014, which application claims priority to U.S. Provisional Application No. 61/888,846, filed on Oct. 9, 2013, the disclosure of which are incorporated herein by reference.

This invention was made with government support under Grant Nos. R01 EY021374 and R01 EY018660 awarded by NIH. The government has certain rights in the invention.

Throughout this application various publications are referenced. The disclosures of these publications in their entireties are hereby incorporated by reference into this application in order to more fully describe the state of the art to which this invention pertains.

BACKGROUND OF THE INVENTION

The leading causes of irreversible blindness include age-related macular degeneration (AMD), retinitis pigmentosa, glaucoma, and retinal vascular diseases, which cause loss of RPE, photoreceptors, retinal ganglion cells (RGCs), and supporting cells in the retina. One potential therapeutic approach is to restore visual function by grafting healthy retinal cells to replace the lost retinal cells. During the past several decades, attempts at using primary retinal progenitor cells isolated from human fetal or adult retinal tissues have met with limited success[1], either due to the low expansion capacity and differentiation potential of adult progenitors or the difficulty of obtaining sufficient human fetal retinal progenitors, raising ethical concerns. Human pluripotent stem cells (hPSCs), including human embryonic stem cells (hESCs), and induced pluripotent stem cells (iPSCs) represent promising renewable donor sources for cell-based replacement therapy. Nevertheless, hPSCs themselves are not suitable for direct transplantation in clinical applications due to their tendency to form teratomas and their low efficiency in repopulating host tissues with desirable reprogrammed cell types in vivo.

Thus, major efforts have focused on production of differentiated derivatives of hPSCs such as neural retinal progenitor cells[2,3], retinal pigment epithelium (RPE)[4-6], and photoreceptors[7-9]. While hESC-derived RPE transplants have now advanced to clinical trials for treatment of patients with Stargardt's macular dystrophy and AMD[10], the effectiveness of RPE grafts may be limited if the majority of photoreceptors have already been lost. Thus, it is highly desirable to develop a renewable retinal stem cell product with the potential to repopulate both RPE and photoreceptors in degenerated retina, yet that poses no risk of forming tumors. Such a product would replace damaged cells and restore visual circuits in conditions where multiple cell types are afflicted.

SUMMARY OF THE INVENTION

The invention provides an in vitro method for producing isolated mammalian primitive retinal stem cells (pRSCs) comprising: (a) culturing isolated embryonic stem cells (ESCs) from a mammal in a cell culture medium that is free of feeder cells, feeder-conditioned medium or serum so as to produce and grow a culture of the isolated ESCs; and (b) contacting the culture of the isolated ESCs so grown with one or more of an inhibitor for Wnt or TGF-β/BMP signaling so as to differentiate the isolated ESCs of (a) into primitive retinal stem cells thereby producing isolated mammalian pRSCs.

The invention further provides an in vitro method for producing isolated mammalian primitive retinal stem cells (pRSCs) comprising: (a) culturing isolated pluripotent stem cells (PSCs) from a mammal in a cell culture medium that is free of feeder cells, feeder-conditioned medium or serum so as to produce and grow a culture of the isolated PSCs; and (b) contacting the culture of the isolated PSCs so grown with one or more of an inhibitor for Wnt or TGF-β/BMP signaling so as to differentiate the isolated PSCs into primitive retinal stem cells, thereby producing isolated mammalian pRSCs.

The invention yet further provides an in vitro method for producing isolated mammalian primitive retinal stem cells (pRSCs) comprising: (a) culturing isolated induced pluripotent stem cells (iPSCs) from a mammal in a cell culture medium that is free of feeder cells, feeder-conditioned medium or serum so as to produce and grow a culture of the isolated iPSCs; and (b) contacting the culture of the isolated iPSCs so grown with one or more of an inhibitor for Wnt or TGF-β/BMP signaling so as to differentiate the isolated iPSCs into primitive retinal stem cells, thereby producing isolated mammalian pRSCs.

The invention additionally provides an in vitro method for producing isolated mammalian retinal ganglion cells (RGCs) comprising: (a) culturing isolated primitive retinal stem cells (pRSCs) from a mammal in a cell culture medium that is free of feeder cells, feeder-conditioned medium or serum so as to produce and grow a culture of the isolated pRSCs; and (b) contacting the culture of the isolated pRSCs so grown with one or more of an inhibitor of Wnt, Notch, or VEGFR signaling so as to differentiate the isolated pRSCs into isolated mammalian RGCs, thereby producing isolated mammalian RGCs.

Also, the invention provides a method for producing isolated mammalian photoreceptors from isolated mammalian pRSCs comprising: (a) culturing and growing dissociated pRSCs from a mammal in a neural induction medium comprising one or more of an inhibitor of a TGF-β/Activin receptor-like kinases ALK-4, -5 or -7, glycogen synthase kinase-3 (GSK-3), Notch or Wnt signaling or an activator of a hedgehog signaling for a sufficient time to induce pRSCs to a photoreceptor cell lineage fate without visible morphological changes or expression of photoreceptor-specific markers; and (b) followed by, culturing and growing pRSCs of step a) in neural induction medium comprising retinoic acid or taurine or both so as to differentiate the mammalian pRSCs to photoreceptors, thereby producing isolated mammalian photoreceptors; wherein the culture medium is free of feeder cells, feeder-conditioned medium or serum.

Further additionally, the invention provides a method for producing non-neural isolated mammalian retinal pigment epithelium (RPE) or isolated mammalian retinal pigment epithelial cells (RPEs) comprising: (a) culturing pRSCs from a mammal in culture medium comprising nicotinamide or activin A or both in absence of SMAD signaling inhibitor for a sufficient time so as to direct pRSCs toward RPE fate; and (b) culturing the pRSCs in culture medium comprising one or more of a N1 medium supplement, taurine, hydrocortisone, or triiodo-thyronin; so as to differentiate the mammalian pRSCs to mammalian RPE or RPEs, thereby, producing isolated mammalian RPE or RPEs, wherein the medium is free of feeder cells or feeder-conditioned medium.

The invention yet further provides a method for production of isolated human primitive retinal stem cells (hpRSCs) from isolated human embryonic stem cells (hESCs) comprising: (a) culturing isolated hESCs on a solid support with culture medium in the absence of feeder cells, feeder-conditioned medium or serum for a sufficient time so as to grow nearly confluent, preferably to about 80% cellular confluence; (b) culturing the isolated hESCs so grown on a solid support in a culture medium comprising basic FGF (bFGF) for a sufficient time so as to grow nearly confluent; (c) culturing the isolated hESCs of step (b) on a solid support with a culture medium comprising a combination of small molecule inhibitors for Wnt and TGF-β/BMP signaling activities so as to differentiate the isolated hESCs to isolated human primitive retinal stem cells, thereby, producing isolated hpRSCs.

Further still, the invention provides a method for production of isolated human primitive retinal stem cells (hpRSCs) from isolated human pluripotent stem cells (hPSCs) comprising: (a) culturing isolated hPSCs on a solid support with culture medium in the absence of feeder cells, feeder-conditioned medium or serum for a sufficient time so as to grow nearly confluent, preferably to about 80% cellular confluence; (b) culturing the isolated hPSCs so grown on a solid support in a culture medium comprising bFGF for a sufficient time so as to grow nearly confluent; (c) culturing the isolated hPSCs of step (b) on a solid support with a culture medium comprising combination of small molecule inhibitors for Wnt and TGF-β/BMP signaling activities so as to differentiate the isolated hPSCs to isolated human primitive retinal stem cells, thereby, producing isolated hpRSCs.

The invention also provides a method for production of isolated human primitive retinal stem cells (hpRSCs) from isolated human induced pluripotent stem cells (iPSCs) comprising: (a) culturing isolated human iPSCs on a solid support with culture medium in the absence of feeder cells, feeder-conditioned medium or serum for a sufficient time so as to grow nearly confluent, preferably to about 80% cellular confluence; (b) culturing the isolated iPSCs so grown on a solid support in a culture medium comprising bFGF for a sufficient time so as to grow nearly confluent; (c) culturing the isolated iPSCs of step (b) on a solid support with a culture medium comprising combination of small molecule inhibitors for Wnt and TGF-β/BMP signaling activities so as to differentiate the isolated iPSCs to isolated human primitive retinal stem cells, thereby, producing isolated hpRSCs.

The invention additionally provides a kit for producing mammalian primitive retinal stem cells (pRSCs) wherein the kit comprises instruction for culturing embryonic stem cells (ESCs), pluripotent stem cells (PSCs) or induced pluripotent stem cells (iPSC) from a mammal in a chemically defined medium, free of feeder cells, feeder-conditioned medium or serum, and instruction for use of small molecular inhibitor for Wnt signaling or TGF-β/BMP signaling or inhibitors for both Wnt and TGF-β/BMP signaling.

DETAILED DESCRIPTION OF THE INVENTION

Figure 1:
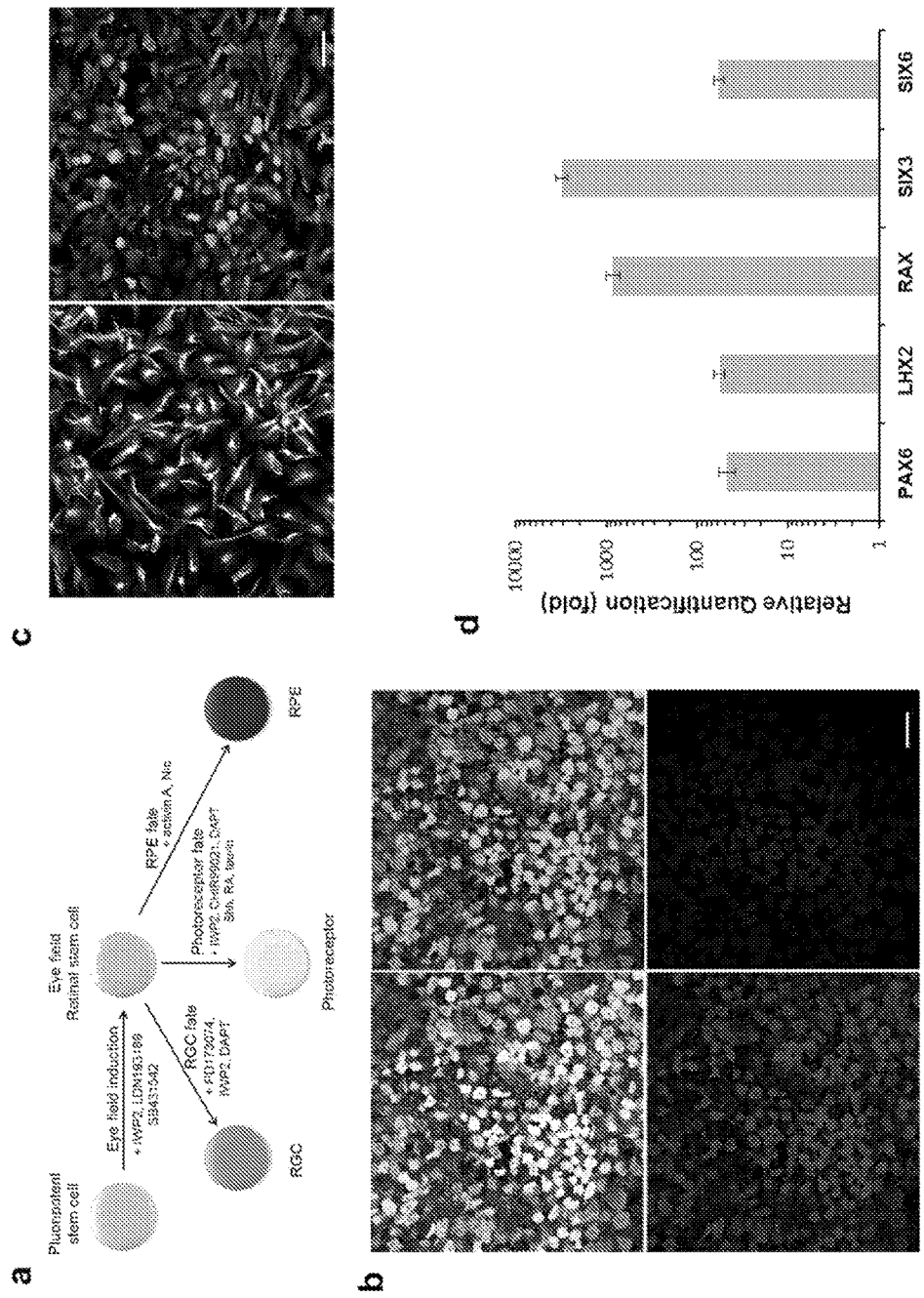
FIG. 1. Induction of hpRSCs from hESCs. (a) A schematic diagramming the directed induction of human retinal cell fates from human pluripotent stem cells in vitro. (b) Confocal images of immunofluorescent labeling of typical early eye field transcription factors PAX6 (green) and LHX2 (red) in hpRSCs derived from hESCs after one week of induction. Cell nuclei were counterstained with Hoechst 33342 (blue). (c) hpRSCs were stained for the neural progenitor/stem cell marker nestin (white) and proliferation marker Ki67 (green). (d) Real-time qPCR analysis of the induced expression of typical early eye field transcription factors. Scale bars=30 μm.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety.

It must be noted that as used herein and in the appended claims, the singular forms "a," "an," and "the" include plural referents unless the context clearly dictates otherwise. Thus, for example, reference to "a formulation" includes a plurality of compounds.

As used herein, the term "about" when used before a numerical designation, e.g., temperature, time, amount, concentration, and such other, including a range, indicates approximations which may vary by (+) or (−) 10%, 5% or 1%.

METHODS OF THE INVENTION

Method for Producing Isolated Mammalian Primitive Retinal Stem Cells (pRSCs)

The invention provides an in vitro method for producing isolated mammalian pRSCs. An advantage of the methods of the invention includes a capability of producing isolated mammalian primitive retinal stem cells in sufficient quantity and quality as to be suitable for cellular transplantation or grafting to an eye of a subject without a need for cellular fractionation or cellular purification prior to cellular transplantation or grafting.

As used herein, isolated pRSCs mean, for example, pRSCs that are substantially separated from contaminants (e.g., such as cells that are not pRSCs).

In one embodiment of the invention, the method comprises culturing isolated embryonic stem cells (ESCs) from a mammal in a cell culture medium that is free of feeder cells, feeder-conditioned medium or serum so as to produce and grow a culture of the isolated ESCs; and contacting the culture of the isolated ESCs with one or more of an inhibitor for Wnt or TGFβ/BMP signaling, so as to differentiate the isolated ESCs into primitive retinal stem cells, thereby producing isolated mammalian pRSCs. In one embodiment, one or more of an inhibitor for Wnt or TGFβ/BMP signaling is a combination of inhibitors for Wnt and TGF-β/BMP signaling. The culture of isolated PSCs may be an adherent culture. In a preferred embodiment, the culture of the isolated ESCs is a monolayer culture. In an embodiment, the culture of the culture of isolated ESCs is grown to near confluence before contacting with one or more of an inhibitor for Wnt or TGFβ/BMP signaling or a combination of inhibitors for Wnt and TGF-β/BMP signaling. In a preferred embodiment, an inhibitor for Wnt or TGFβ/BMP signaling is a small molecule inhibitor.

As used herein, isolated ESCs mean, for example, ESCs that are substantially separated from contaminants (e.g., such as cells that are not ESCs).

As used in the context of the invention, signaling refers to a signaling pathway or pathways where a group of cellular proteins participate to control one or more cell functions. A signal, for example a ligand, activates a signaling pathway through a receptor for the signal, which serves as the first member of the pathway; this interaction between the signal and its receptor initiates a chain of events that lead to subsequent changes in the biological activity or biological states of downstream members, and ultimately to an alteration in cell function. Change in cell function is thus a consequence of a signal activating a signaling pathway associated with the signal. A signal may also activate more than one signaling pathways, such as for example in Wnt or TGF-β signaling. In addition, signaling pathways may show cross-talk through shared members within two or more pathways.

Often, a signaling pathway is named for a ligand protein or signal that activates the pathway, such as Wnt, TGF-β, bone morphogenetic protein (BMP) or hedgehog ligand in Wnt, TGF-β, BMP or hedgehog signaling, respectively. For example, Wnt protein ligand may initiate Wnt signaling upon binding to its receptor, Frizzled; TGF-β protein ligand or members of the TGF-β superfamily of ligands (including Activin and BMP) may initiate TGF-β signaling upon binding to a TGF-β type II receptor and in combination with type I receptor participate in ligand specific signaling for the TGF-β superfamily of ligands; BMP may initiate BMP signaling upon binding to bone morphogenetic protein receptor type-2 (BMPR2); and hedgehog protein ligand may initiate hedgehog signaling upon binding to its receptor, Patched. Alternatively, a signaling pathway may be named for a recipient of a signal or ligand, such as a Notch receptor in Notch signaling, which upon activation transmits its activated status downstream to control one or more cell functions, such as control of gene expression.

Furthermore, in TGF-β signaling, binding of TGF-β superfamily of ligands (such as TGF-β, Activin or BMP) to its respective type II receptor (such as TGF-β receptor type II, Activin receptor type II or BMP receptor type II) may result in receptor activation and subsequent activation of one of seven type I receptors, which fall into two different groups: a TGF-β/Activin subgroup including TGF-β superfamily type I receptor Activin receptor-like kinases, ALK-4, ALK-5 and ALK-7; and a BMP subgroup including ALK-1, ALK-2, ALK-3, and ALK-6 type I receptors. Both of these different subgroups are involved in the regulation of SMAD family of transcriptional factors to regulate gene transcription.

Equivalent in the context of the invention refers to equivalent compounds or substitutes that could serve the same or similar function as the compounds or substances being replaced. Such equivalence may be determined on the basis of ability to inhibit or activate a particular signaling pathway (as the compound being replaced or the preferred or most preferred compound being replaced), using a similar assay as used to characterize the compound. Most preferred compounds of the invention are: IWP2 for inhibition of Wnt signaling, SB431542 for inhibition of TGF-β superfamily type I activin receptor-like kinases ALK-4, ALK-5 and ALK-7, LDN-193189 for inhibition of BMP type I receptors ALK-2 and ALK-3, DAPT for inhibition of Notch signaling, PD173074 for inhibition of VEGFR signaling, CHIR99021 for inhibition of glycogen synthase kinase-3, purmorphamine for activation of hedgehog signaling, or retinoic acid for activating retinoic acid signaling (such as through RAR complexes).

A defined medium or chemically defined medium refers to the fact that the medium is essentially free of ill-defined components, such as serum and feeder-conditioned medium. A chemically defined medium may be produced with chemical components, including deionized or distilled water. It may include purified proteins, such as growth factors and serum proteins such as albumin, preferably recombinant proteins, amino acids (essential and/or non-essential), vitamins, salts, lipids, sugar, pyruvate, buffer, trace metal, reducing agent, and indicator dye. Further, the medium may be supplemented with hormone, receptor ligand, metabolite, amino sulfonic acid, inhibitory factors, morphogens, cell signaling molecules, and activators or inhibitors of cell signaling or kinase activity. The use of a defined medium or chemically defined medium to culture cells is advantageous for cell-based replacement therapy.

In accordance with the practice of the invention, the monolayer culture may be grown until nearly confluent, near confluency, or confluent. In an embodiment, nearly confluent or near confluency may be about 70% confluence or confluency, preferably about 80% confluence or confluency. Further culturing of an about 80% confluent cell culture and growth of such a culture may be described as nearly confluent or near confluency, wherein confluence may be about 90% or greater. At confluence, cells are packed with entire culture surface covered by cells and all cells are in contact with each other. Further, in one embodiment of the invention, the cultured cells may be cultured or grown using a solid support. Optionally, the solid support may be coated with Matrigel® or basement membrane. Further, the Matrigel® or basement membrane may be growth factor-reduced Matrigel® or reduced growth factor basement membrane. In an alternative embodiment, the solid support may be coated with a reduced growth factor basement membrane and grown in a tissue culture plate, tray, flask, or microbeads coated with growth factor-reduced Matrigel® (BD Biosciences), Geltrex® LDEV-Free hESC-qualified Reduced Growth Factor Basement Membrane Matrix or equivalent or mixtures thereof.

In one embodiment of the invention, the method comprises culturing isolated pluripotent stem cells (PSCs) from a mammal in a cell culture medium that is free of feeder cells, feeder-conditioned medium or serum so as to produce and grow a culture of the isolated PSCs; and contacting the culture of the isolated PSCs with one or more of an inhibitor for Wnt or TGF-β/BMP signaling so as to differentiate the isolated PSCs into pRSCs, thereby producing isolated mammalian pRSCs. In one embodiment, one or more of an inhibitor for Wnt or TGFβ/BMP signaling is a combination of inhibitors for Wnt and TGF-β/BMP signaling. The culture of isolated PSCs may be an adherent culture. In a preferred embodiment, the culture of the isolated ESCs is a monolayer culture. In an embodiment, the culture of the culture of isolated PSCs is grown to near confluence before contacting with one or more of an inhibitor for Wnt or TGFβ/BMP signaling or a combination of inhibitors for Wnt and TGF-β/BMP signaling. In a preferred embodiment, an inhibitor for Wnt or TGFβ/BMP signaling is a small molecule inhibitor. In accordance with the practice of the invention, the induced pluripotent stem cells (iPSCs) from a mammal may be similarly treated in place of isolated PSCs to produce isolated mammalian pRSCs.

As used herein, isolated PSCs mean, for example, PSCs that are substantially separated from contaminants (e.g., such as cells that are not PSCs).

As used herein, isolated iPSCs mean, for example, iPSCs that are substantially separated from contaminants (e.g., such as cells that are not iPSCs).

In one embodiment, the method of the invention produces isolated mammalian primitive retinal stem cells at more than about 90% efficiency within, for example, about 7 days of treatment with one or more of an inhibitor for Wnt or TGF-β/BMP signaling or a combination of inhibitors for Wnt and TGF-β/BMP signaling. In a preferred embodiment, an inhibitor for Wnt or TGF-β/BMP signaling is a small molecule inhibitor.

A small molecule is a low molecular weight organic compound that is less than 900 daltons, preferably around 500 daltons or less. For example, in some embodiment, a small molecule used in the invention has molecular weight of 466.6 daltons for IWP2, 384.39 daltons for SB431542, 406.48 daltons for LDN-193189, 465.34 daltons for CHIR-99021, 432.46 daltons for DAPT, 523.67 for PD173074 or 520.62 daltons for purmorphamine. A small molecule binds to specific protein or nucleic acid to alter the activity or function of the protein or nucleic acid. As such, a small molecule has biological activity and may regulate a biological process.

As used in the context of the invention, a small molecule inhibitor is an inhibitor of a cellular signaling pathway. A small molecule inhibitor may work by competing with the activating signal such as binding of a ligand or protein ligand to its receptor. It may work by preventing protein-protein interactions required for propagation of the activating signal. It may work to inhibit the activity of any one of the members of the signaling pathway, so as to disrupt the transmission of an activating signal through the pathway. For example, a small molecule inhibitor such as SB431542 by selectively and potently inhibiting the activity of TGF-β superfamily type I ALK-4, -5, and -7 receptors, which are downstream of the type II receptors to which Activin or TGF-β binds, further blocks signaling of Activin or TGF-β to SMAD2 and SMAD3 transcription factors.

Unlike a small molecule inhibitor, a small molecule activator of a signaling pathway, referred to also as small molecule activator of signaling (e.g., Wnt, TGF-β/BMP, Notch, VEGFR, hedgehog, or SMAD signaling), modulates the signaling pathway by activating the pathway. Similar to a small molecule inhibitor of signaling or signaling pathway, a small molecule activator of signaling or signaling pathway may activate the pathway at any step or position in the pathway through various members of the pathway. While often it may be desirable to activate the signaling pathway at the beginning of the pathway through agonist ligand interaction with specific receptor, this need not necessarily be the case. In the case of a small molecule activator of hedgehog signaling, purmorphamine activates downstream of the hedgehog signaling pathway by acting as an agonist for Smoothened, a critical component in hedgehog signaling.

A modulator of a signaling pathway may be an activator or inhibitor of a signaling pathway. It may be a small molecule.

In the practice of the invention, the preferred embodiment of inhibitor, activator or modulator for signaling or a kinase is a small molecule inhibitor, small molecule activator or small molecule modulator for signaling or a kinase.

Synergistic inhibition of Wnt and TGF-β/BMP signaling or signaling activities refers to a result of inhibiting Wnt signaling and inhibiting TGF-β and BMP signaling in which the result is more than just an additive result of inhibiting Wnt signaling alone and result of inhibiting TGF-β and BMP signaling alone. Synergism may arise due to interaction between components of Wnt signaling and TGF-β and BMP signaling, such as for example formation of a transcription factor complex between β-catenin and Lef1/Tcf (downstream components of Wnt signaling) and Smad4 (a coSMAD and an essential mediator of TGF-β and BMP signaling), resulting in synergistic activation of target genes (Nishita et al., Nature 403, 781-785 (2000)).

Examples of small molecule inhibitors for the Wnt signaling include, but are not limited to, inhibitor of Wnt Production-1 (IWP-1), Inhibitor of Wnt Production-2 (IWP2), JW55, JW74, okadaic acid, tautomycin, SB239063, SB203580, ADP-HPD, 2-[4-(4-fluorophenyl) piperazin-1-yl]-6-methylpyrimidin-4(3H)-one, PJ34, cambinol, sulindac, 3289-8625, scaffold A for series of analogs designed to inhibit Dishevelled protein, scaffold B for series of analogs designed to inhibit Dishevelled protein, J01-017a, NSC668036, filipin, IC261, PF670462, Bosutinib, PHA665752, Imatinib, ICG-001, ethacrynic acid, ethacrynic acid derivative, PKF115-584, PNU-74654, PKF118-744, CGP049090, PKF118-310, ZTM000990, BC21, GDC-0941, Rp-8-Br-cAMP, LGK974, C59, Ant 1.4Br/Ant 1.4CI, niclosamide, apicularen, bafilomycin, XAV939, IWR1, pyrvinium, NSC668036, 2,4-diamino-quinazoline, quercetin, and PKF115-584, and equivalent and combination thereof.

Merely by way of example, the inhibitor for the Wnt signaling may be a small molecule inhibitor of Wnt Production-2 or a Dkk1 analog. Suitable examples of the small molecule inhibitor of Wnt Production-2 or Dkk1 analog include, but are not limited to, an Inhibitor of Wnt Production-2 (IWP2; CAS No. 686770-61-6) or N-(6-methyl-1,3-benzothiazol-2-yl)-2-[(4-oxo-3-phenyl-6,7-dihydrothieno[3,2-d]pyrimidin-2-yl)sulfanyl]acetamide having a chemical formula of $C_{22}H_{18}N_4O_2S_3$ and a chemical structure of:

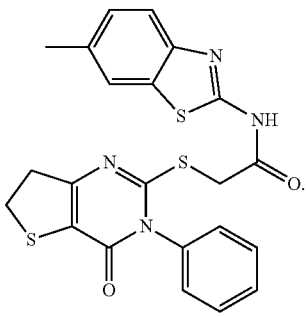 [SMILES: Cc1ccc2nc(NC(=O)CSc3nc4c(c(=O)n3-c3ccccc3)SCC4)sc2c1]

Suitable examples of the small molecule inhibitor for the TGF-β/BMP signaling include, but are not limited to, SB431542 (4-[4-(1,3-benzodioxol-5-yl)-5-(2-pyridinyl)-1H-imidazol-2-yl]benzamide), A 83-01 (3-(6-Methyl-2-pyridinyl)-N-phenyl-4-(4-quinolinyl)-1H-pyrazole-1-carbothioamide), SJN 2511 (2-(3-(6-Methylpyridine-2-yl)-1H-pyrazol-4-yl)-1,5-naphthyridine), D 4476 (4-[4-(2,3-Dihydro-1,4-benzodioxin-6-yl)-5-(2-pyridinyl)-1H-imidazol-2-yl]benzamide), LY 364947 (4-[3-(2-Pyridinyl)-1H-pyrazol-4-yl]-quinoline), SB 525334 (6-[2-(1,1-Dimethylethyl)-5-(6-methyl-2-pyridinyl)-1H-imidazol-4-yl]quinoxaline), SD 208 (2-(5-Chloro-2-fluorophenyl)-4-[(4-pyridyl)amino]pteridine), and LDN-193189 (4-(6-(4-(piperazin-1-yl)phenyl)pyrazolo[1,5-a]pyrimidin-3-yl) quinoline) and equivalent and combination thereof.

In one embodiment, the inhibitor for TGF-β/BMP signaling also may be a small molecule inhibitor of the transforming growth factor-beta (TGF-β) superfamily type I activin receptor-like kinases ALK-4, -5, or -7. In a preferred embodiment, the inhibitor for TGF-β/BMP signaling also may be a small molecule inhibitor of the transforming growth factor-beta (TGF-β) superfamily type I activin receptor-like kinases ALK-4, -5, and -7.

Further, a small molecule inhibitor of the transforming growth factor-beta (TGF-β) superfamily type I activin receptor-like kinases ALK-4, -5, and -7 may be or may comprise SB431542 (CAS No. 301836-41-9) or 4-[4-(1,3-benzodioxol-5-yl)-5-(2-pyridinyl)-1H-imidazol-2-yl]benzamide having a chemical formula of $C_{22}H_{16}N_4O_3$ and a chemical structure of

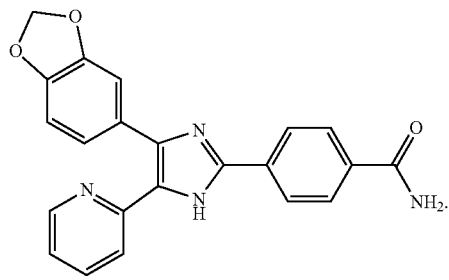 [SMILES: NC(=O)c1ccc(-c2nc(-c3ccc4c(c3)OCO4)c(-c3ccccn3)[nH]2)cc1]

Additionally, the inhibitor for TGF-β/BMP signaling may be or may comprise a small molecule inhibitor of BMP type I receptors ALK-2 or ALK-3 or a noggin analog. In a preferred embodiment, the inhibitor for TGF-β/BMP signaling may be or may comprise a small molecule inhibitor of BMP type I receptors ALK-2 and ALK-3 or a noggin analog Also, the small molecule inhibitor of BMP type I receptors ALK-2 and ALK-3 or a noggin analog may be or may comprise LDN-193189 (CAS No. 1062368-24-4) or 4-(6-(4-(piperazin-1-yl)phenyl)pyrazolo[1,5-a]pyrimidin-3-yl) quinoline having a chemical formula of $C_{25}H_{22}N_6$ and a chemical structure of

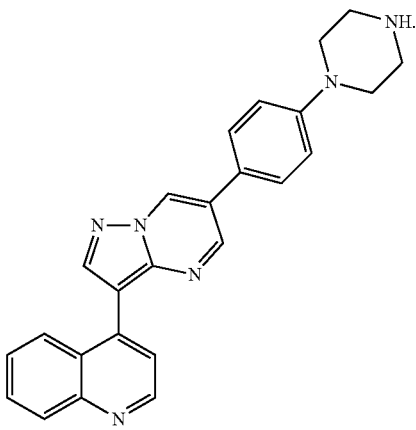 [SMILES: c1ccc2c(-c3cnn4cc(-c5ccc(N6CCNCC6)cc5)cnc34)ccnc2c1]

Further, the combination of inhibitors for Wnt and TGF-β/BMP signaling may be or may comprise a combination of: (a) one or more inhibitors of Wnt Production-2 or Dkk1 analog; (b) one or more inhibitors of transforming growth factor-beta (TGF-β) superfamily type I activin receptor-like kinases ALK-4, -5, and -7; and (c) one or more inhibitors of BMP type I receptors ALK-2 and ALK-3 or a noggin analog, wherein the combination includes inhibitors for at least two signaling pathways or preferably inhibitors for all three signaling pathways. The inhibitors may be small molecules.

Further still, the combination of inhibitors for Wnt and TGF-β/BMP signaling activities may be a combination of at least two, and preferably all three, of IWP2 (CAS No. 686770-61-6), SB431542 (CAS No. 301836-41-9), and LDN-193189 (CAS No. 1062368-24-4) or an equivalent combination wherein the combination produces synergistic inhibition of Wnt and TGF-β/BMP signaling activities; or a combination comprising at least two, and preferably all three, of IWP2 (CAS No. 686770-61-6), SB431542 (CAS No. 301836-41-9), and LDN-193189 (CAS No. 1062368-24-4) or an equivalent combination wherein the combination produces synergistic inhibition of Wnt and TGF-β/BMP signaling activities.

In one embodiment of the invention, the isolated mammalian primitive retinal stem cells, may be at over about 90% of total cell population, and are positive for both PAX6 and LHX2 transcription factors expressed by eye field progenitors.

In another embodiment, the isolated mammalian primitive retinal stem cells may be positive for expression of PAX6, LHX2, RAX, OTX2, SIX3 and/or SIX6 typical early eye field transcription factors.

In a further embodiment, the isolated mammalian primitive retinal stem cells may be positive for expression of stemness factors SOX2, nestin and STAT3 typical markers of primitive neuroepithelial stem cells.

In yet a further embodiment, the isolated mammalian primitive retinal stem cells may be positive for expression of Ki67, a marker for cellular proliferation.

In a further embodiment, the isolated mammalian primitive retinal stem cells downregulates transcription of ESC pluripotency transcription factors, POU5F1 (OCT4), NANOG, KLF4 and TBX3 genes, and TBF-β superfamily genes, SMAD1, SMAD2, TGFβ3, BMP3, BMP6, TGFBR1, and BMPR1B, compared with ESCs.

In a further embodiment, the isolated mammalian primitive retinal stem cells maintain transcription of LIN28 and SALL4 transcription factor genes to the same level as in ESCs but at a significantly higher level than in fetal retinal progenitor cells.

In a further embodiment, the isolated mammalian primitive retinal stem cells upregulates transcription of BMP4 and BMP7 genes and OTX2, RAX, LHX2, SIX3, and SIX6 genes compared with fetal retinal progenitor cells.

In a further embodiment, the isolated mammalian primitive retinal stem cells are strongly positive for transcription of SRFP1 and FZD3/5 genes.

In a further embodiment, the isolated mammalian primitive retinal stem cells downregulates transcription of FGFR1/2/3 and FGF3/8 genes compared with fetal retinal progenitor cells.

In a further embodiment, the isolated mammalian pRSCs are directed to differentiate toward specific retinal cell fates in vitro using small molecule inducers of differentiation.

In a further embodiment, the specific retinal cell fates include neuroretinal cells and non-neuronal cells.

In a further embodiment, the neuroretinal cells include retinal ganglion cells (RGCs) and photoreceptors.

In a further embodiment, the non-neuronal cells include cells of retinal pigment epithelium (RPE) or retinal pigment epithelial cells (RPEs).

Examples of Suitable Cell Culture Media

In one embodiment, one or more defined medium/media with or without supplement(s) comprise: DMEM/F12 or equivalent medium; Glutamine or L-alanyl-L-glutamine (GlutaMAX®); StemPro® hESC Supplement or equivalent; Bovine serum albumin or equivalent; Basic fibroblast growth factor (bFGF-basic) or equivalent; and 2-mercaptoethanol or equivalent.

In another embodiment, one or more defined medium/media with or without supplement(s) comprises: DMEM/F12 or equivalent medium; about 2.3 mM Glutamine or L-alanyl-L-glutamine (GlutaMAX®); 1× StemPro® hESC Supplement or equivalent; about 1.8% Bovine serum albumin or equivalent; about 8 ng/mL Basic fibroblast growth factor (bFGF-basic) or equivalent; and about 0.1 mM 2-mercaptoethanol or equivalent.

In yet a further embodiment, one or more defined medium/media with or without supplement(s) may be serum-free N2B27 priming medium comprising: DMEM/F12 or equivalent medium; N-2 supplement or equivalent; B-27 Serum-Free Supplement or equivalent; Glutamine or L-alanyl-L-glutamine (GlutaMAX®); Bovine serum albumin or equivalent; MEM non-essential amino acids or equivalent; and 2-mercaptoethanol or equivalent. Additionally, one embodiment of the medium is serum free N2B27 priming medium supplemented with basic fibroblast growth factor (bFGF-basic) or equivalent. Further, in another embodiment, the medium may comprise DMEM/F12 or equivalent medium; 1×N-2 supplement or equivalent; 1×B-27 Serum-Free Supplement or equivalent; about 2 mM Glutamine or L-alanyl-L-glutamine (GlutaMAX®); about 0.2% Bovine serum albumin or equivalent; about 0.1 mM MEM non-essential amino acids or equivalent; and about 0.1 mM 2-mercaptoethanol or equivalent. Additionally, another embodiment of the medium is serum free N2B27 priming medium supplemented with about 20 ng/mL basic fibroblast growth factor (bFGF-basic) or equivalent.

In one embodiment, the defined medium with or without supplement(s) may further comprise IWP2 (CAS No. 686770-61-6), SB431542 (CAS No. 301836-41-9), or LDN-193189 (CAS No. 1062368-24-4) or equivalents. In a preferred embodiment, the defined medium with or without supplement(s) may further comprise at least two, and preferably all three, of IWP2 (CAS No. 686770-61-6), SB431542 (CAS No. 301836-41-9), or LDN-193189 (CAS No. 1062368-24-4) or equivalents.

In one embodiment, one or more defined medium/media with or with supplement(s) may further comprise about 1 μM IWP2, about 5 μM SB431542 or about 50 nM LDN193189. In a preferred embodiment, one or more defined medium/media with or with supplement(s) may further comprise at least two, and preferably all three, of about 1 μM IWP2, about 5 μM SB431542 and about 50 nM LDN193189.

In another embodiment, a defined medium may be serum-free N2B27 priming medium supplemented with one or more of an inhibitor for Wnt or TGF-β/BMP signaling, or more preferably, a combination of small molecule inhibitors for Wnt and TGF-β/BMP signaling. Further, the medium may contain or may not contain supplement(s) and does not contain feeder cells, feeder-conditioned medium or serum. Further still, the medium may additionally comprise a combination of small molecule inhibitors for Wnt and TGF-β/BMP signaling. In a preferred embodiment, the medium may comprise DMEM/F12 or equivalent medium; N-2 supplement or equivalent; B-27 Serum-Free Supplement or equivalent; Glutamine or L-alanyl-L-glutamine (GlutaMAX®); Bovine serum albumin or equivalent; MEM non-essential amino acids or equivalent; 2-mercaptoethanol or equivalent; and one or more preferably a combination of at least two, most preferably all three, of IWP2 (CAS No. 686770-61-6) or equivalent; SB431542 (CAS No. 301836-41-9) or equivalent; and LDN-193189 (CAS No. 1062368-24-4) or equivalents.

In a more preferred embodiment, the defined medium is a priming medium supplemented with one or more of an inhibitor for Wnt or TGF-β/BMP signaling, or more preferably, a combination of small molecule inhibitors for Wnt and TGF-β/BMP signaling activities and further comprise DMEM/F12 or equivalent medium; 1×N-2 supplement or equivalent; 1×B-27 Serum-Free Supplement or equivalent; about 2 mM Glutamine or L-alanyl-L-glutamine (GlutaMAX®); about 0.2% Bovine serum albumin or equivalent; about 0.1 mM MEM non-essential amino acids or equivalent; about 0.1 mM 2-mercaptoethanol or equivalent; and one or more preferably a combination of at least two, most preferably all three, of about 1 μM IWP2 (CAS No. 686770-61-6) or equivalent; about 5 μM SB431542 (CAS No. 301836-41-9) or equivalent; and about 50 nM LDN-193189 (CAS No. 1062368-24-4) or equivalents.

In one embodiment, the isolated mammalian pRSCs may be maintained and/or expanded in serum-free N2B27 priming medium supplemented with a combination of small molecule inhibitors for Wnt and TGF-β/BMP signaling activities of the invention.

In Vitro Methods for Producing Isolated Mammalian Retinal Ganglion Cells (RGCs)

The invention yet further provides an in vitro method for producing isolated mammalian retinal ganglion cells (RGCs). The method comprises culturing isolated primitive retinal stem cells (pRSCs) from a mammal in a cell culture medium that is free of feeder cells, feeder-conditioned medium or serum so as to produce and grow a monolayer culture of the isolated pRSCs; and contacting the culture of the isolated pRSCs with one or more of an inhibitor of Wnt, Notch, or VEGFR signaling, so as to differentiate the isolated pRSCs into isolated mammalian RGCs. In one embodiment, the cells may be cultured on a solid support. The solid support may be coated, e.g., with Matrigel® or basement membrane or equivalent. The Matrigel® or basement membrane may be growth factor-reduced Matrigel® or growth factor-reduced basement membrane. In an embodiment of the invention, the cells may be cultured and allowed to grow and proliferate for over two weeks.

As used herein, isolated RGCs mean, for example, RGCs that are substantially separated from contaminants (e.g., such as cells that are not RGCs).

The inhibitors of Wnt, Notch, or VEGFR signaling may be a small molecule inhibitor. In one embodiment, one or more of an inhibitor of Wnt, Notch or VEGFR signaling is a combination of inhibitors for at least two signaling pathways. Optionally, combination may include inhibitors for all three signaling pathway.

In one embodiment, the culture of the isolated pRSCs is a monolayer culture. Further, the monolayer culture may be nearly confluent or confluent.

In one embodiment, the cell culture medium that is free of feeder cells, feeder-conditioned medium or serum is a chemically defined medium. The chemically defined medium may be N2B27 priming medium or equivalent, free of feeder cells, feeder-conditioned medium or serum.

In an embodiment, the combination of inhibitors of Wnt, Notch, and VEGFR signaling may be IWP2, DAPT, and PD173074, respectively. The IWP2, DAPT, and PD173074 may be used at a concentration of about 1 μM IWP2, about 10 μM DAPT, and about 200 nM PD173074.

In one embodiment, the isolated mammalian pRSCs may be cultured for over 2 weeks in a chemically defined medium supplemented with small molecule inhibitors of Wnt, Notch, and VEGFR signaling to obtain isolated mammalian RGCs.

In one embodiment, upregulation of RGC precursor-specific transcription factor genes may occur after about the first six days of culture in a chemically defined medium supplemented with small molecule inhibitors of Wnt, Notch, and VEGFR signaling. Upregulation of RGC precursor-specific transcription factor genes may comprise BRN3A, BRN3B, ISL-1 and MATH5, compared with ESCs.

In one embodiment, majority of cells in culture may be positive for markers of RGCs after 2 weeks in a chemically defined medium supplemented with small molecule inhibitors of Wnt, Notch, and VEGFR signaling. Further, majority of cells in culture positive for markers of RGCs may be positive for TUJ1 and BRN3.

Method for Producing Isolated Mammalian Photoreceptors

The invention also provides a method for producing isolated mammalian photoreceptors from isolated mammalian pRSCs under chemically defined condition in vitro, free of feeder cells, feeder-conditioned medium or serum, wherein such method may comprise culturing and growing dissociated pRSCs from a mammal in neural induction medium supplemented with one or more of inhibitors of TGF-β/Activin receptor-like kinases ALK-4, -5 or -7, glycogen synthase kinase-3 (GSK-3), Notch or Wnt signaling or an activator of hedgehog signaling. For example, culturing and growing dissociated pRSCs in a neural induction medium for sufficient time may induce pRSCs to a photoreceptor cell lineage fate without visible morphological changes or expression of photoreceptor-specific markers. In one embodiment, the cells may be cultured on a solid support. The solid support may be coated, e.g., with Matrigel® or basement membrane or equivalent. The Matrigel® or basement membrane may be growth factor-reduced Matrigel® or growth factor-reduced basement membrane. In an embodiment of the invention, the cells may be cultured and allowed to grow and proliferate for about 6 days.

As used herein, isolated photoreceptors mean, for example, photoreceptors that are substantially separated from contaminants (e.g., such as cells that are not photoreceptors).

For example, one or more of inhibitors of TGF-β/Activin receptor-like kinases ALK-4, -5 or -7, glycogen synthase kinase-3 (GSK-3), Notch or Wnt signaling or an activator of hedgehog signaling may be a combination of inhibitors of TGF-β/Activin receptor-like kinases ALK-4, -5 and -7, glycogen synthase kinase-3 (GSK-3), Notch and Wnt signaling and an activator of hedgehog signaling which may include modulators for at least two signaling pathways. Optionally, and more preferably, combination may include modulators for all five signaling pathways. In the case of one or more of an inhibitor of TGF-β/Activin receptor-like kinases ALK-4, -5 or -7, glycogen synthase kinase-3 (GSK-3), Notch or Wnt signaling, the one or more of an inhibitor may be a combination of inhibitors of TGF-β/Activin receptor-like kinases ALK-4, -5 and -7, glycogen synthase kinase-3 (GSK-3), Notch and Wnt signaling, wherein the combination includes inhibitors for at least two signaling pathways or preferably inhibitors for all four signaling pathways. The inhibitor of TGF-β/Activin receptor-like kinases ALK-4, -5 and -7, glycogen synthase kinase-3 (GSK-3), Notch or Wnt signaling or an activator of hedgehog signaling may be a small molecule inhibitor.

Following this first culture step, the method further comprises culturing the cells in neural induction medium supplemented with retinoic acid or equivalent, or taurine or equivalent, or both, so as to differentiate the mammalian pRSCs to photoreceptor cells, thereby producing isolated mammalian photoreceptors from isolated pRSCs from a mammal under defined cell culture condition in vitro, free of feeder cells, feeder-conditioned medium or serum. In a further embodiment, the cells may be cultured for about 7 days or longer or for a period that permits the pRSCs to differentiate to photoreceptor cells.

In a preferred embodiment, the methods for producing isolated mammalian photoreceptors from isolated mammalian pRSCs under chemically defined condition in vitro, free of feeder cells, feeder-conditioned medium or serum may comprise: culturing pRSCs on a solid support coated with Matrigel® or basement membrane or equivalent (wherein Matrigel® or basement membrane is growth factor reduced) in neural induction medium supplemented with small molecule inhibitors of TGF-β/Activin receptor-like kinases ALK-4, -5 and -7, glycogen synthase kinase-3 (GSK-3), Notch and Wnt signaling and a small molecule activator of hedgehog signaling; and followed by, culturing in neural induction medium supplemented with retinoic acid or equivalent, and taurine or equivalent; so as to differentiate the mammalian pRSCs to photoreceptors, thereby, producing isolated mammalian photoreceptors from isolated pRSCs from a mammal under defined cell culture condition in vitro, free of feeder cells, feeder-conditioned medium or serum.

In a further preferred embodiment, the cells may be cultured for about 6 days, followed by cell culturing for about 7 days or longer so as to differentiate the mammalian pRSCs to photoreceptor cells. After culturing, photoreceptors may be obtained from pRSCs. The photoreceptors so obtained may express pan-photoreceptor marker recoverin, cone cell-specific marker OPN1SW or blue opsin, rod cell-specific marker rhodopsin, and/or interphotoreceptor retinoid binding protein (IRBP). Further, the photoreceptors may display cellular processes, short inner processes and/or long extended outer processes.

In one embodiment, the isolated mammalian photoreceptors are positive for rhodopsin, rhodopsin kinase and/or transmucin.

In an alternative embodiment, isolated mammalian photoreceptors may be obtained from isolated mammalian pRSCs by culturing and growing dissociated pRSCs from a mammal in a neural induction medium comprising one or more of an inhibitor of a TGF-b/Activin receptor-like kinases ALK-4, -5 or -7, glycogen synthase kinase-3 (GSK-3), Notch or Wnt signaling or an activator of a hedgehog signaling for a sufficient time to induce pRSCs to a photoreceptor cell lineage fate without visible morphological changes or expression of photoreceptor-specific markers. The cells in culture are contacted with a retinoic acid or taurine or both so as to differentiate the mammalian pRSCs to photoreceptor cells. The culture medium is free of feeder cells, feeder-conditioned medium or serum. Cells are grown on a solid support, which may be coated with Matrigel® or basement membrane, preferably growth factor-reduced Matrigel® or growth factor-reduced basement membrane.

Suitable examples of neural induction culture media include the following:

A neural induction medium may comprise Advanced DMEM/F12 medium or equivalent; Neurobasal® medium or equivalent; N2 supplement or equivalent; B-27 Serum-Free Supplement or equivalent; Glutamine or L-alanyl-L-glutamine (e.g., GlutaMAX®); Bovine serum albumin or equivalent; and human leukemia inhibitory factor (hLIF) or equivalent.

A preferred neural induction medium may comprise Advanced DMEM/F12:Neurobasal (about 1:1) medium or equivalent; N2 supplement (e.g., about 1×N2 supplement) or equivalent; B-27 Serum-Free Supplement (e.g., about 1×B-27 Serum-Free Supplement) or equivalent; Glutamine (e.g., about 1% Glutamine) or L-alanyl-L-glutamine (GlutaMAX®); Bovine serum albumin (e.g., about 5 ug/mL Bovine serum albumin) or equivalent; and human leukemia inhibitory factor (hLIF) (e.g., about 10 ng/mL hLIF) or equivalent.

In a medium, examples of small molecule inhibitors of TGF-β/Activin receptor-like kinases ALK-4, -5 and -7, glycogen synthase kinase-3 (GSK-3), Notch and Wnt signaling and the small molecule activator of hedgehog signaling include, but are not limited to, SB431542 (CAS No. 301836-41-9) or equivalent, CHIR99021 (CAS No. 252917-06-9) or equivalent, DAPT (CAS No. 208255-80-5) or equivalent, IWP2 (CAS No. 686770-61-6) or equivalent, and purmorphamine (CAS No. 483367-10-8) or equivalent, respectively.

As a supplement to a neural induction medium, any one or more of the following may be added, SB431542 (CAS No. 301836-41-9) or equivalent, CHIR99021 (CAS No. 252917-06-9) or equivalent, DAPT (CAS No. 208255-80-5) or equivalent, IWP2 (CAS No. 686770-61-6) or equivalent, and purmorphamine (CAS No. 483367-10-8) or equivalent. Merely by way of example, the supplement may be added at a concentration of about 2 µM SB431542 (CAS No. 301836-41-9) or equivalent; about 3 µM CHIR99021 (CAS No. 252917-06-9) or equivalent; about 10 µM DAPT (CAS No. 208255-80-5) or equivalent; about 1 µM IWP2 (CAS No. 686770-61-6) or equivalent; and about 100 nM purmorphamine (CAS No. 483367-10-8) or equivalent.

In a further embodiment, retinoic acid or equivalent, and taurine or equivalent may be used to supplement a neural induction medium at a concentration of about 500 nM retinoic acid or equivalent; and/or about 100 µM taurine or equivalent.

Method for Producing Non-Neural Isolated Mammalian Retinal Pigment Epithelium (RPE) or Isolated Mammalian Retinal Pigment Epithelial Cells (RPEs)

The invention additionally provides a method for producing non-neural isolated mammalian retinal pigment epithelium (RPE) from isolated mammalian pRSCs in vitro, free of feeder cells or feeder-conditioned medium. Optionally, the method may be used to obtain isolated mammalian retinal pigment epithelial cells (RPEs) from isolated mammalian pRSCs in vitro, free of feeder cells and feeder-conditioned medium. In an embodiment of the invention, the method comprises culturing monolayer of pRSCs from a mammal in RPE induction medium supplemented with nicotinamide or equivalent, or activin A or equivalent, or both; and followed by, culturing the pRSCs in culture medium supplemented with a N1 medium supplement or equivalent, taurine or equivalent, hydrocortisone or equivalent, or triiodo-thyronin or equivalent; so as to differentiate the mammalian pRSCs to mammalian RPE or RPEs from isolated pRSCs of a mammal in vitro, free of feeder cells or feeder-conditioned medium. For example, mammalian pRSCs may be cultured in a medium with nicotinamide or activin A or both in absence of SMAD signaling inhibition for a sufficient time so as to direct pRSCs toward RPE fate.

As used herein, isolated RPEs mean, for example, RPEs that are substantially separated from contaminants (e.g., such as cells that are not RPEs).

In one embodiment, the pRSCs may be cultured in an RPE medium supplemented with a N1 medium supplement, taurine, hydrocortisone, and triiodo-thyronin.

In one embodiment of the methods, the pRSC cells (e.g., from a mammal) may be cultured on a solid support. The solid support may be coated with Matrigel® or basement membrane or equivalent.

The Matrigel® or basement membrane may be growth factor-reduced Matrigel® or growth factor-reduced basement membrane. The medium used for culture may be RPE induction medium supplemented with nicotinamide or equivalent, or Activin A or equivalent, or both in absence of SMAD signaling inhibitor for about 7 days to direct pRSCs toward RPE fate.

In another embodiment, cells may be cultured in RPE medium supplemented with N1 medium supplement or equivalent, taurine or equivalent, hydrocortisone or equivalent, or triiodo-thyronin or equivalent for about 12 days or longer. pRSCs then differentiate to RPE fate. In yet another embodiment, cells may be cultured in RPE induction medium supplemented with nicotinamide or equivalent, and activin A or equivalent for about 7 days, followed by culturing in RPE medium supplemented with N1 medium supplement or equivalent, taurine or equivalent, hydrocortisone or equivalent, and triiodo-thyronin or equivalent for about 12 days or longer. Following culturing in RPE medium supplemented with N1 medium supplement or equivalent, taurine or equivalent, hydrocortisone or equivalent, and triiodo-thyronin or equivalent for about 12 days or longer, RPE or RPEs may be obtained from pRSCs. The RPE or RPEs may express RPE65, form polygonal actin bundles and may become pigmented.

In a preferred embodiment, the method for producing non-neural isolated mammalian retinal pigment epithelium (RPE) or isolated mammalian retinal pigment epithelial cells (RPEs) from isolated mammalian pRSCs in vitro, free of feeder cells and feeder-conditioned medium may comprise: culturing monolayer of pRSCs in RPE induction medium supplemented with nicotinamide or equivalent, and activin A or equivalent; and followed by, culturing in RPE maturation medium supplemented with N1 medium supplement or equivalent, taurine or equivalent, hydrocortisone or equivalent, and triiodo-thyronin or equivalent; so as to differentiate the mammalian pRSCs to mammalian RPE or RPEs, thereby, producing isolated mammalian RPE or RPEs from isolated pRSCs of a mammal in vitro, free of feeder cells and feeder-conditioned medium.

In a separate embodiment, the method for producing non-neural isolated mammalian RPE or RPEs from isolated mammalian pRSCs in vitro, free of feeder cells and feeder-conditioned medium may comprise: culturing pRSCs from a mammal in culture medium comprising nicotinamide or activin A or both in absence of SMAD signaling inhibitor and contacting the pRSCs with one or more of a N1 medium supplement, taurine, hydrocortisone or triiodo-thyronin; so as to differentiate the mammalian pRSCs to mammalian RPE or RPEs, thereby producing isolated mammalian RPE or RPEs from isolated pRSCs of a mammal in vitro, free of feeder cells and feeder-conditioned medium.

Suitable examples of RPE induction culture medium and RPE medium include the following: RPE induction medium may comprise Glasgow Minimum Essential Medium (GMEM) or equivalent; KnockOut™ serum replacement or equivalent; MEM non-essential amino acids or equivalent; Sodium pyruvate or equivalent; and β-mercaptoethanol or equivalent.

A preferred example of RPE induction medium comprises Glasgow Minimum Essential Medium (GMEM) or equivalent; KnockOut™ serum replacement (e.g., about 10% KnockOut™ serum replacement) or equivalent; MEM non-essential amino acids (e.g., about 0.1 mM MEM non-essential amino acids) or equivalent; Sodium pyruvate (e.g., about 1 mM Sodium pyruvate) or equivalent; and β-mercaptoethanol (e.g., about 0.1 mM β-mercaptoethanol) or equivalent.

Nicotinamide or equivalent, and/or activin A or equivalent may be present in a RPE induction medium at a concentration of e.g., about 10 mM nicotinamide or equivalent; and/or about 100 ng/mL activin A or equivalent.

A RPE medium may comprise Minimum Essential Medium (αMEM) Alpha Modification Medium or equivalent; Fetal bovine serum or equivalent; L-glutamine or L-alanyl-L-glutamine (GlutaMAX®); MEM non-essential amino acids or equivalent; and Sodium pyruvate or equivalent.

A preferred example of an RPE medium may comprise Minimum Essential Medium (αMEM) Alpha Modified Medium or equivalent; about 5% Fetal bovine serum or equivalent; about 2 mM L-glutamine or L-alanyl-L-glutamine (GlutaMAX®); about 0.1 mM MEM non-essential amino acids or equivalent; and about 1 mM Sodium pyruvate or equivalent.

In one embodiment, the RPE medium may comprise N1 medium supplement or equivalent, taurine or equivalent, hydrocortisone or equivalent, and triiodo-thyronin or equivalent. Further, in a preferred embodiment, the RPE medium may comprise 1×N1 medium supplement or equivalent; about 0.25 mg/mL taurine or equivalent; about 20 ng/mL hydrocortisone or equivalent; and about 0.013 ng/mL triiodo-thyronin or equivalent.

Method for Production of Isolated Human Primitive Retinal Stem Cells (hpRSCs)

The invention further provides a method for production of isolated human primitive retinal stem cells (hpRSCs) from isolated human embryonic stem cells (hESCs), isolated human pluripotent stem cells (hPSCs), or isolated human induced pluripotent stem cells (iPSCs) under defined cell culture condition in vitro, free of feeder cells, feeder-conditioned medium or serum. In one embodiment, the method comprises (a) culturing isolated hESCs, isolated hPSCs, or isolated human iPSCs on a solid support coated with growth factor-reduced Matrigel (BD Bioscience) or its equivalent in StemPro hESC SFM medium (Invitrogen) or its equivalent in the absence of feeder cells, feeder-conditioned medium or serum to near confluence, preferably to about 80% cellular confluence; (b) culturing in a priming medium supplemented with basic FGF (bFGF) for a sufficient time so as to grow nearly confluent; (c) culturing in a priming medium supplemented with a combination of small molecule inhibitors for Wnt and TGF-β/BMP signaling activities, so as to differentiate the isolated hESCs, isolated hPSCs or isolated human iPSCs to isolated human primitive retinal stem cells.

In a preferred embodiment, the method for production of isolated human primitive retinal stem cells (hpRSCs) may comprise: culturing isolated hESCs, isolated hPSCs, or isolated human iPSCs on a solid support coated with growth factor-reduced Matrigel® (BD Bioscience) or its equivalent in StemPro hESC SFM medium (Invitrogen) or its equivalent in the absence of feeder cells, feeder-conditioned medium or serum; switching StemPro hESC SFM medium near about 80% cellular confluence to a serum-free N2B27 priming medium supplemented with about 20 ng/mL bFGF wherein the serum-free N2B27 priming medium may comprise: DMEM/F12 or equivalent, 1×N-2 supplement or equivalent, 1×B-27 Serum-Free Supplement or equivalent, about 0.2% BSA or equivalent, about 2 mM L-GlutaMAX® or equivalent, about 0.1 mM MEM non-essential amino acids or equivalent, and about 0.1 mM β-mercaptoethanol or equivalent); culturing in N2B27 priming medium supplemented with bFGF for about 1-2 days; switching the medium supplemented with bFGF in N2B27 priming medium for a nearly confluent monolayer culture of hESCs to N2B27 priming medium supplemented with a combination of small molecule inhibitors for Wnt and TGF-β/BMP signaling activities, so as to differentiate the isolated hESCs, isolated hPSCs or isolated human iPSCs to isolated human primitive retinal stem cells, thereby, producing isolated hpRSCs from isolated hESCs, isolated hPSCs, or isolated human iPSCs under defined cell culture condition in vitro, free of feeder cells, feeder-conditioned medium or serum.

In one embodiment, the combination of small molecule inhibitors for Wnt and TGF-β/BMP signaling activities in the medium may be a combination of SB 431542, LDN193189 and IWP2 (Inhibitor of Wnt Production-2); a combination of SB 431542, a noggin analog and IWP2; a combination of SB 431542, LDN193189 and a Dkk1 analog; a combination of SB 431542, a noggin analog and a Dkk1 analog; or an equivalent combination wherein the combination produces synergistic inhibition of Wnt and TGF-β/BMP signaling activities. In a preferred embodiment, the combination of SB 431542, LDN193189 and IWP2 may comprise about 5 µM SB 431542, about 50 nM LDN193189, and about 1 µM IWP2.

In one embodiment, the isolated human primitive retinal stem cells, at over about 90% of total cell population, may be positive for PAX6, LHX2 RAX, OTX2, SIX3 and SIX6 typical early eye field transcription factors expressed by eye field progenitors. In another embodiment, the isolated human primitive retinal stem cells may be positive for expression of stemness factors SOX2, nestin and STAT3 typical markers of primitive neuroepithelial stem cells. In yet another embodiment, the isolated human primitive retinal stem cells may be positive for expression of Ki67, a marker for cellular proliferation.

In one embodiment, the isolated human primitive retinal stem cells may downregulate transcription of hESC pluripotency transcription factors, POU5F1 (OCT4), NANOG, KLF4 and TBX3 genes, and TBF-β superfamily genes, SMAD1, SMAD2, TGFβ3, BMP3, BMP6, TGFBR1, and BMPR1B, compared with hESCs.

In an embodiment of the invention, the isolated human primitive retinal stem cells may maintain transcription of LIN28 and SALL4 transcription factor genes to the same level as in hESCs but at a significantly higher level than in human fetal retinal progenitor cells.

In another embodiment, the isolated human primitive retinal stem cells may upregulate transcription of BMP4 and BMP7 genes and OTX2, RAX, LHX2, SIX3, and SIX6 genes compared with human fetal retinal progenitor cells.

In an embodiment of the invention, the isolated human primitive retinal stem cells may be strongly positive for transcription of SRFP1 and FZD3/5 genes.

In one embodiment, the isolated human primitive retinal stem cells may downregulate transcription of FGFR1/2/3 and FGF3/8 genes compared with human fetal retinal progenitor cells.

In an embodiment, the isolated human pRSCs may be maintained and/or expanded in serum-free N2B27 priming medium supplemented with a combination of small molecule inhibitors for Wnt and TGF-β/BMP signaling activities of the invention.

In another embodiment, the isolated human pRSCs may be directed to differentiate toward specific retinal cell fates in vitro using small molecule inducers of differentiation.

In one embodiment, the specific retinal cell fates may include neuroretinal cells and non-neuronal cells. The neuroretinal cells may include retinal ganglion cells (RGCs) and photoreceptors. The non-neuronal cells may include retinal pigment epithelium (RPE) cells.

Methods for Generating Mammalian Primitive Retinal Stem Cells (hpRSCs), More Differentiated Retinal Progenitors, Retinal Neurons, Retinal Ganglion Cells, Photoreceptor Precursor, or Retinal Pigmented Epithelium (RPE)

The invention further provides a method for generating mammalian primitive retinal stem cells (hpRSCs), more differentiated retinal progenitors, retinal neurons, retinal ganglion cells, photoreceptor precursor, or retinal pigmented epithelium (RPE) from a subject requiring the production of induced pluripotent stem cells (iPSC) from the subject and generation of pRSCs from iPSC by the method of the invention, and/or additionally further induction of differentiation by a method of the invention.

Method for Treating Retinal Degeneration in a Subject

The invention additionally provides a method for treating retinal degeneration in a subject in need thereof comprising administering primitive retinal stem cells, retinal ganglion cells, photoreceptors, retinal pigment epithelium cells and/or combination thereof to an eye of the patient. The primitive retinal stem cells, retinal ganglion cells, photoreceptors, retinal pigment epithelium cells may be administered in a sufficient amount so as to treat the retinal degeneration in the subject and may be produced by the method of the invention.

As used herein, the terms "subject" or "patient" may be used interchangeably and refer to any living organism which can be administered any derived compositions of the present invention. The term includes, but is not limited to, humans, non-human animals, for example non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. Thus, adult and newborn subjects, as well as fetuses, whether male or female, are intended to be covered.

The term "effective amount" as used herein refers to the amount of e.g., the cells of the invention and/or a composition required to retard, reduce or ameliorate at least one symptom of an eye-related disease or disorder, e.g., retinal degeneration. For example, an effective amount of any of the cells of the invention is the amount of effective to reduce or inhibit retinal degeneration of the cells of the invention. Thus, an effective amount is also the amount sufficient to prevent the development of an eye-related disease symptom, or to reduce a symptom or reduce the rate of symptom progression.

As used herein, the terms "administering" and "introducing" are used interchangeably herein and refer to the placement of cells or compositions of the invention as disclosed herein into a subject by a method or route which results in at least partial localization of the cells or compositions at a desired site. The cells or compositions of the present invention can be administered by any appropriate route which results in an effective treatment in the subject.

In one embodiment, the cells to be delivered may be combined with or contained on or in a matrix, e.g., a hydrogel, prior to delivery to the eye of the patient.

In one embodiment, the hydrogel may comprise hyaluronic acid and methylcellulose or salts and derivatives thereof. Further, the hydrogel may comprise a hydrogel with a bioactive peptide. In one embodiment, the matrix may be a biocompatible polymer or mixture of biocompatible polymers which support cell viability and functionality of transplanted cells, artificial biomimetic matrix, bioactive scaffold derived from tissue or organ matrix, biosynthetic extracellular matrix based on collagen and N-isopropylacrylamide copolymers, or scaffolds modified with adhesion molecule, lamin, growth factor, morphogenetic factor, survival factor, extracellular matrix or fragment or derivative. The hydrogel may comprise about 0.5% sodium hyaluronate (1400-1800 kDa) and about 0.5% methylcellulose (100 kDa) or their equivalence in a balanced salt solution.

In one embodiment, the cells may be administered to subretinal space of the eye of the subject.

In an embodiment, retinal degeneration may be associated with age-related macular degeneration (AMD), Stargardt's macular dystrophy, retinitis pigmentosa, glaucoma, retinal vascular disease, viral infection of the eye, and other retinal/ocular disease of known or unknown etiology.

In accordance with the practice of the invention, the subject may be a mammal such as a human. The subject may also be a mammal such as monkey, bear, rat, mouse, mink, rabbit, guinea pig, pig, dog, cat, goat, sheep, horse or cow.

In one embodiment, the method for treating a retinal degeneration in a subject in need thereof comprises (a) obtaining a tissue or cell sample containing PSCs and somatic cells from the subject; (b) separating the PSCs and somatic cells from the sample so as to obtain isolated PSCs and isolated somatic cells; (c) culturing isolated PSCs so as to grow the isolated PSCs; or, reprogramming isolated somatic cells so as to obtain iPSCs and isolating iPSCs so as to obtain isolated iPSCs; (d) culturing the isolated PSCs or isolated iPSCs so as to produce pRSCs by the method of the invention; and (e) administering primitive retinal stem cells (pRSCs) to an eye of the subject in a sufficient amount so as to treat the retinal degeneration in the subject.

In another embodiment, the method for treating a retinal degeneration in a subject in need thereof comprises (a) obtaining a tissue or cell sample containing PSCs and somatic cells from the subject; (b) separating the PSCs and somatic cells from the sample so as to obtain isolated PSCs and isolated somatic cells; (c) culturing isolated PSCs so as to grow the isolated PSCs; or, reprogramming isolated somatic cells so as to obtain iPSCs and isolating iPSCs so as to obtain isolated iPSCs; (d) culturing the isolated PSCs or isolated iPSCs so as to produce pRSCs; (e) culturing the isolated pRSCs so as to produce isolated RGCs by the method of the invention; and (f) administering mammalian retinal ganglion cells (RGCs) so produced to an eye of the subject in a sufficient amount so as to treat the retinal degeneration in the subject.

In a further embodiment, the method for treating a retinal degeneration in a subject in need thereof comprises (a) obtaining a tissue or cell sample containing PSCs and somatic cells from the subject; (b) separating the PSCs and somatic cells from the sample so as to obtain isolated PSCs and isolated somatic cells; (c) culturing isolated PSCs so as to grow the isolated PSCs; or, reprogramming isolated somatic cells so as to obtain iPSCs and isolating iPSCs so as to obtain isolated iPSCs; (d) culturing the isolated PSCs or isolated iPSCs so as to produce pRSCs; (e) culturing the isolated pRSCs so as to produce isolated photoreceptors by the method of the invention; and (f) administering the photoreceptors of step (e) to an eye of the subject in a sufficient amount so as to treat the retinal degeneration in the subject.

In yet further embodiment, the method for treating a retinal degeneration in a subject in need thereof comprises (a) obtaining a tissue or cell sample containing PSCs and somatic cells from the subject; (b) separating the PSCs and somatic cells from the sample so as to obtain isolated PSCs and isolated somatic cells; (c) culturing isolated PSCs so as to grow the isolated PSCs; or, reprogramming isolated somatic cells so as to obtain iPSCs and isolating iPSCs so as to obtain isolated iPSCs; (d) culturing the isolated PSCs or isolated iPSCs so as to produce pRSCs; (e) culturing the isolated pRSCs so as to produce isolated RPE's by the method of the invention; and (f) administering mammalian retinal pigment epithelium cells (RPEs) so produced to an eye of the subject in a sufficient amount so as to treat the retinal degeneration in the subject.

Methods for Delivery of Human Primitive Retinal Stem Cells (hpRSCs), Human Primitive Retinal Ganglion Cells (hpRGCs), Human Photoreceptors or Human Retinal Pigment Epithelial Cells (hRPEs) to a Subject The invention further additionally provides a method for delivery of human primitive retinal stem cells (hpRSCs), human primitive retinal ganglion cells (hpRGCs), human photoreceptors or human retinal pigment epithelial cells (hRPEs) to a patient or subject in need, wherein single cell suspension of hpRSCs, hpRGCs, human photoreceptors or hRPEs in, e.g., a BSS/HAMC (about 0.5/0.5% w/w) hydrogel solution is administered into the subretinal space of a subject.

In one embodiment, the invention provides a method for treating retinal degeneration in a patient or subject in need requiring the delivery of primitive retinal stem cells (pRSCs) to an eye of the patient or subject in need, wherein the pRSCs may be produced by the method the invention.

In one embodiment, the invention provides a method for treating retinal degeneration in a patient or subject in need requiring the delivery of mammalian retinal ganglion cells (RGCs) to an eye of the patient or subject in need, wherein the RGCs may be produced by the method of the invention.

In one embodiment, the invention provides a method for treating retinal degeneration in a patient or subject in need requiring the delivery of mammalian photoreceptors to an eye of the patient or subject in need, wherein the photoreceptors may be produced by the method of the invention.

In one embodiment, the invention provides a method for treating retinal degeneration in a patient or subject in need requiring the delivery of mammalian retinal pigment epithelium (RPE) or mammalian retinal pigment epithelial cells (RPEs) to an eye of the patient or subject in need, wherein the RPEs may be produced by a method of the invention.

The mammal may be a human, monkey, bear, rat, mouse, mink, rabbit, guinea pig, pig, dog, cat, goat, sheep, horse or cow.

The subject or patient may be a human. In an embodiment, the subject or patient may be a mammal such as a human, monkey, bear, rat, mouse, mink, rabbit, guinea pig, pig, dog, cat, goat, sheep, horse or cow.

The invention also provides methods for delivery of human primitive retinal stem cells (hpRSCs), human retinal ganglion cells (hpRGCs), human photoreceptors, human retinal pigment epithelium (hRPE) or human retinal pigment epithelial cells (hRPEs) to a patient. In one embodiment, hpRSCs, hpRGCs, human photoreceptors, hRPE or hRPEs may be administered as a monolayer or single cell suspension in a matrix solution or matrix suspension into the subretinal space of the subject. The cells may be produced by the method of the invention. In one embodiment, the single cell suspension of hpRSCs in a BSS/HAMC (about 0.5/0.5% w/w) hydrogel solution may be administered into the subretinal space of a patient. Delivery of the cells may be to a subject in need and may be for treating a retinal degeneration.

In one embodiment, the matrix is a hydrogel which comprises hyaluronic acid and methylcellulose or salts and derivatives thereof, a hydrogel with a bioactive peptide, a biocompatible polymer or mixture of biocompatible polymers which support cell viability and functionality of transplanted cells, artificial biomimetic matrix, bioactive scaffold derived from tissue or organ matrix, biosynthetic extracellular matrix based on collagen and N-isopropylacrylamide copolymers, or scaffolds modified with adhesion molecule, lamin, growth factor, morphogenetic factor, survival factor, extracellular matrix or fragment or derivative.

In one embodiment, the invention provides methods for determining molecular and cellular events that underlie pathogenesis of retinal degeneration of a subject requiring generation of human primitive retinal stem cells (hpRSCs), more differentiated retinal progenitors, retinal neurons, retinal ganglion cells, photoreceptor precursor, or retinal pigmented epithelium (RPE) from a subject by the method of the invention to obtain "disease in a dish" model so as to be able to determine molecular and cellular events that underlie pathogenesis of retinal degeneration in a subject.

In one embodiment, the subject is a mammal, human, monkey, bear, rat, mouse, mink, rabbit, guinea pig, pig, dog, cat, goat, sheep, horse or cow.

In an embodiment, the invention provides methods for preventing or inhibiting tumors associated with the use of pluripotent stem cells to treat a subject afflicted with retinal degeneration. The method comprises inducing isolated pluripotent stem cells to isolated hpRSCs and administering isolated hpRSCs produced to the subject, wherein the isolated pRSC may be produced by a method of the invention before administering stem cells to eye of the subject.

In another embodiment, the method comprises inducing isolated pluripotent stem cells to isolated hpRSCs, further differentiating the isolated hPRSCs to isolated hpRGCs, isolated human photoreceptors or isolated hRPEs and administering isolated hpRSCs, isolated human photoreceptors or isolated hRPEs produced to the subject.

Compositions of the Invention

The invention provides a composition comprising mammalian primitive retinal stem cells (hpRSCs) produced by the method of the invention and a suitable carrier.

The phrase "suitable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, or be biologically inert.

Further, the invention provides a composition comprising mammalian retinal ganglion cells (RGCs) produced by a method of the invention and a suitable carrier.

Further still, the invention provides a composition comprising mammalian photoreceptors produced by the method of the invention and a suitable carrier.

The invention also provides a composition comprising mammalian retinal pigment epithelium (RPE) or mammalian retinal pigment epithelium cells (RPEs) produced by the method of the invention and a suitable carrier.

In one embodiment, the combination of small molecular inhibitors for Wnt and TGF-β/BMP signaling activities may be a combination of IWP2 (CAS No. 686770-61-6), SB431542 (CAS No. 301836-41-9), and LDN-193189 (CAS No. 1062368-24-4) or an equivalent combination wherein the combination may produce synergistic inhibition of Wnt and TGF-β/BMP signaling activities. Alternatively, the combination may comprise IWP2 (CAS No. 686770-61-6), SB431542 (CAS No. 301836-41-9), and/or LDN-193189 (CAS No. 1062368-24-4) or an equivalent combination wherein the combination may produce synergistic inhibition of Wnt and TGF-β/BMP signaling activities.

In one embodiment, the mammal is a human, monkey, bear, rat, mouse, mink, rabbit, guinea pig, pig, dog, cat, goat, sheep, horse or cow.

According to another aspect of the invention, kits are provided. Kits according to the invention include package(s) comprising compounds or compositions of the invention.

The phrase "package" means any vessel containing compounds or compositions presented herein. In preferred embodiments, the package can be a box or wrapping. Packaging materials for use in packaging pharmaceutical products are well known to those of skill in the art.

The kit can also contain items that are not contained within the package but are attached to the outside of the package, for example, pipettes.

Kits may optionally contain instructions for administering compositions of the present invention to a subject having a condition in need of treatment. Kits may also comprise instructions for approved uses of compounds herein by regulatory agencies, such as the United States Food and Drug Administration. Kits may optionally contain labeling or product inserts for the present compounds. The package(s) and/or any product insert(s) may themselves be approved by regulatory agencies. The kits can include compounds in the solid phase or in a liquid phase (such as buffers provided) in a package. The kits also can include buffers for preparing solutions for conducting the methods, and pipettes for transferring liquids from one container to another.

The kit may optionally also contain one or more other compounds for use in combination therapies as described herein. In certain embodiments, the package(s) is a container for intravenous administration. In other embodiments, compounds are provided in an inhaler. In still other embodiments compounds are provided in a polymeric matrix or in the form of a liposome.

In one embodiment, the invention provides kits for producing mammalian primitive retinal stem cells (pRSCs) of a subject requiring treatment of adherent monolayer of pluripotent stem cells (PSCs) or induced pluripotent stem cells (iPSC) from a subject in vitro using a chemically defined medium, free of feeder cells, feeder-conditioned medium or serum, but supplemented with one or more of an inhibitor for Wnt or TGF-β/BMP signaling, or more preferably supplemented with a combination of small molecular inhibitors for Wnt and TGF-β/BMP signaling.

The invention further provides kits for producing mammalian primitive retinal stem cells (pRSCs) wherein the kit comprises instruction for culturing embryonic stem cells (ESCs), pluripotent stem cells (PSCs) or induced pluripotent stem cells (iPSC) from a mammal in a chemically defined medium, free of feeder cells, feeder-conditioned medium or serum, and instruction for use of small molecular inhibitors for Wnt signaling or TGF-β/BMP signaling or inhibitors for both Wnt and TGF-β/BMP signaling.

In one embodiment, the kit further includes small molecule inhibitor for Wnt signaling or TGF-β/BMP signaling or small molecule inhibitors for both Wnt and TGF-β/BMP signaling.

In one embodiment, the small molecule inhibitor for Wnt signaling may comprise an Inhibitor of Wnt Production-2 (IWP2; CAS No. 686770-61-6) or N-(6-methyl-1,3-benzothiazol-2-yl)-2-[(4-oxo-3-phenyl-6,7-dihydrothieno[3,2-d]pyrimidin-2-yl)sulfanyl]acetamide having a chemical formula of $C_{22}H_{18}N_4O_2S_3$.

In one embodiment, the small molecule inhibitor for TGF-β/BMP signaling may be a small molecule inhibitor of the transforming growth factor-beta (TGF-β) superfamily type I activin receptor-like kinases ALK-4, -5, and -7. The small molecule inhibitor of the transforming growth factor-beta (TGF-β) superfamily type I activin receptor-like kinases ALK-4, -5, and -7 may be SB431542 (CAS No. 301836-41-9) or 4-[4-(1,3-benzodioxol-5-yl)-5-(2-pyridinyl)-1H-imidazol-2-yl]benzamide having a chemical formula of $C_{22}H_{16}N_4O_3$.

In one embodiment, the small molecule inhibitor for TGF-β/BMP signaling may be a small molecule inhibitor of BMP type I receptors ALK-2 and ALK-3 or a noggin analog. The small molecule inhibitor of BMP type I receptors ALK-2 and ALK-3 or a noggin analog may be LDN-193189 (CAS No. 1062368-24-4) or 4-(6-(4-(piperazin-1-yl)phenyl)pyrazolo[1,5-a]pyrimidin-3-yl)quinoline having a chemical formula of $C_{25}H_{22}N_6$.

In one embodiment, small molecular inhibitors for both Wnt and TGF-β/BMP signaling may be a combination of IWP2 (CAS No. 686770-61-6), SB431542 (CAS No. 301836-41-9), and LDN-193189 (CAS No. 1062368-24-4) or an equivalent combination wherein the combination may produce synergistic inhibition of Wnt and TGF-β/BMP signaling activities. Alternatively, the combination may comprise IWP2 (CAS No. 686770-61-6), SB431542 (CAS No. 301836-41-9), and LDN-193189 (CAS No. 1062368-24-4) or an equivalent combination wherein the combination may produce synergistic inhibition of Wnt and TGF-β/BMP signaling activities.

In one embodiment, the kit may further include embryonic stem cells (ESCs), pluripotent stem cells (PSCs) or induced pluripotent stem cells (iPSC) from a mammal. The kit may further include chemically defined culture medium and/or supplements.

In one embodiment, kit may be produced comprising an instruction sheet for use and based on any of the method or composition used in the invention as disclosed in the application or the claims. Such kits may include kits for production of RPGs, photoreceptors, RPE or RPEs from pRGCs of the invention and may include medium, supplement(s), small molecule inhibitor(s) and/or small molecule activator(s).

The following examples are intended to illustrate the present invention, not to limit the scope of the invention in any way.

EXAMPLES

Example 1

Methods
Cell Culture and Differentiation.
Human embryonic stem cells, H9 (WA9, WiCell) and HuES9 (http://grants.nih.gov/stem_cells/registry/current.ht-m?id=40) (passage 25-40), were cultured under feeder-free and serum-free conditions in StemPro hESC SFM medium (Invitrogen) on plates coated with growth factor-reduced Matrigel (BD Biosciences). Human primary fetal retinal progenitors were isolated from 17-week human fetal retina obtained with informed consent and IRB approval and cultured following a previously described procedure[45]. After the undifferentiated hESCs reached ~80% confluence in culture, the medium was switched to serum-free N2B27 priming medium (DMEM/F12, N2, B27, 0.2% BSA, 2 mM L-GlutaMAX, 0.1 mM MEM non-essential amino acids, and 0.1 mM β-mercaptoethanol) supplemented with 20 ng/ml bFGF for 1-2 days. The nearly confluent monolayer culture of hESCs was further cultured in N2B27 priming medium supplemented with small molecule inhibitors (5 μM SB431542, 50 nM LDN193189, and 1 μM IWP2). The medium was changed daily for six days. The hESC-derived hpRSCs may be maintained and expanded in this serum-free, inhibitor-supplemented priming medium. To induce RGC differentiation from hpRSCs, the cells were cultured in the priming medium supplemented with a new combination of small molecule inhibitors including 1 μM IWP2, 10 μM DAPT, and 200 nM PD173074 for over two weeks. For photoreceptor precursor differentiation, dissociated hpRSCs were plated on a Matrigel-coated plate and cultured in neural induction medium as described previously[18] and supplemented with 1 μM IWP2, 10 μM DAPT, and 100 nM purmorphamine for six days. Subsequently, the culture was shifted to neural induction medium supplemented with 500 nM retinoic acid and 100 μM taurine for another week. For RPE differentiation, the RPE induction medium (GMEM, 10% knockout serum replacement, 0.1 mM MEM non-essential amino acids, 1 mM Na-Pyruvate, and 0.1 mM β-mercaptoethanol) supplemented with 10 mM nicotinamide and 100 ng/ml activin A was added to the monolayer culture of hpRSCs for one week. Subsequently, the RPE precursors were matured in RPE medium, consisting of MEM-a modified medium, 5% fetal bovine serum, 2 mM L-glutamine, 0.1 mM MEM non-essential amino acids, and 1 mM Na-Pyruvate, supplemented with N1 and THT (Taurine, Hydrocortisone, Triiodo-thyronin)[46].

PCR analysis. Total RNA was extracted from cells using the RNeasy kit (Qiagen), and cDNA was reverse-transcribed using the iScript cDNA Synthesis kit (Bio-Rad), both following the manufacturers' instructions. The transcripts were amplified for 40 cycles and their levels quantified using gene-specific primers (Table 1) and Power SYBR Green PCR Master Mix on the 7500 Real-Time PCR System (Applied Biosystems). Measurements were performed in triplicate and normalized to β-actin levels.

TABLE 1

Primers used for real-time qPCR

| Gene | Forward Primer | Reverse Primer |
| --- | --- | --- |
| β-ACTIN | GCGAGAAGATGACC CAGATC | CCAGTGGTACGGCC AGAGG |
| BRN3A | CTACACGCACGAAC TGAG | AACACGCAGACAGA ACAA |
| BRN3B | AGCGCTCTCACTTA CCCTTACACA | AAATGGTGCATCGG TCATGCTTCC |
| ISL-1 | GGTTGCGGCAATCA GATTCAC | TTGGCGCATTTGAT CCCGTAC |

TABLE 1-continued

Primers used for real-time qPCR

| Gene | Forward Primer | Reverse Primer |
|---|---|---|
| LHX2 | GCACCACCAGCTTCGGACCA | ACCAGACCTGGAGGACCCGC |
| MATH5 | AGTGGGGCCAGGATAAAAAG | GGAACGGGAGGTAGTGGTC |
| PAX6 | TGTCCAACGGATGTGTGAGT | TTTCCCAAGCAAAGATGGAC |
| RAX | TTTCACCACGTACCAGCTGCA | TCATGGAGGACACTTCCAGCT |
| SIX3 | CGGAGCCTGTTGCGGGAGTG | ATGCCGCTCGGTCCAATGGC |
| SIX6 | ACCCCTACGCAGGTGGGCAA | TGAAGTGGCCGCCTTGCTGG |

Transcriptome and Pathway Data Analysis.

Gene expression data produced in this study (hfRPC and hpRSC) and obtained from the GEO database[47] (HuES9, GSM1001748[48]) were normalized and subjected to average linkage hierarchical clustering using the Cluster 3.0/Tree View software package[49]. 4359 genes were used, based on minimal log 2=1.5 distance between samples with the highest and lowest expression. Total distance (similarity) between samples was calculated as uncentered Pearson correlation coefficients. For each gene in a heat map, red and blue colors denote high and low expression relative to other cells, respectively. For the analyses of individual pathways, subsets of genes in the TGFβ superfamily, Wnt pathway, Notch pathway, hESC pluripotency, Hedgehog pathway, and FGF pathway were selected based on previous studies[50-54]. Clustering was performed with the same parameters with each subset of genes separately.

Immunocytochemistry.

Cells were fixed with 4% paraformaldehyde for 20 min, permeabilized with 0.3% Triton X-100-PBS for 5 min twice, and blocked in a solution of PBS containing 5% normal donkey serum and 0.3% TritonX-100%, followed by an overnight incubation in primary antibody solutions at 4° C. After three washes in PBS, cells were incubated with Alexa fluorescently conjugated secondary antibodies for another 90 min. After rinses and washes in PBS, cell nuclei were counterstained with 100 ng/ml Hoechst 33342 for 10 min. Primary antibodies and their working dilutions were as follow: sheep anti-Chx10 (1:300, Exalpha), rabbit anti-Pax6 (1:600, Covance), goat anti-Lhx2 (1:200, Santa Cruz), rabbit anti-recoverin (1:2000, Millipore), mouse anti-rhodopsin (1:250, Millipore), rabbit anti-red/green opsin (1:300, Millipore), goat anti-OPN1SW (1:300, Santa Cruz), and rabbit anti-GFP (1:1000, Invitrogen) or chicken anti-GFP (1:400, Invitrogen). Mouse anti-HSA antibodies are a mixture of monoclonal antibodies against human-specific marker TRA-1-85 (1:100, R&D Systems), human nuclear antigen (1:300, Millipore), and human mitochondria (1:100, Millipore). The secondary antibodies used were the corresponding Alexa-488, -555, -633, or -647 fluorescent-labeled antibodies (1:1000, Invitrogen). Labeled cells were imaged with a laser-scanning confocal microscope (Olympus). The specific immunoreactivity of each antibody was confirmed by immunostaining with appropriate retinal tissues as positive controls under the same conditions.

Cell Transplantation.

Subretinal transplantation into the rat eye was adapted from the method described previously[55]. Briefly, hpRSCs were dissociated into single cells with StemPro Accutase (Invitrogen) and concentrated to a density of $5 \times 10^4/\mu L$ in either balanced salt solution (BSS, Alcon) only or BSS/HAMC (0.5/0.5% w/w) hydrogel solution[56]. To prepare the HAMC hydrogel solution, sodium hyaluronate (HA, 1400-1800 kDa, Pharma Grade 150, Novamatrix) was sterilized by dissolving in water (HyClone, Cell Culture Grade, Thermo Scientific) at 0.1% w/v and filtering through a 0.22 μm Tube-Top Vacuum Filter (Corning). The solution was then freeze-dried in sterile conditions by covering the tubes with 0.22 um PVDF filters (Millex GV, Millipore). Methylcellulose (MC, 100 kDa, Methocel A4M Premium, Dow Chemical) was dissolved in water at 0.3% w/v by stirring in an ice bath, and was then sterile-filtered and lyophilized as for HA. Sterile HA and MC powders were resuspended in BSS in a biosafety cabinet (e.g. for 0.5%/0.5% HAMC, dissolved 30 mg HA and 30 mg MC in 6 mL BSS), and the suspension was then vortexed, left at 4° C. overnight to solubilize, and vortexed again before use. With a glass micropipette, 1-2 μl of hpRSCs ($5$-$10 \times 10^4$ cells) in suspension were slowly injected into the subretinal space of either nude rats or RCS rats. At different time points post-transplantation, the animals were sacrificed, and the eyes were enucleated and embedded in tissue freezing medium, cryosliced, and co-immunostained as described above. Animal procedures were conducted with the approval and under the supervision of the Institutional Animal Care and Use Committee at the University of California, San Diego.

Results

Induction of hpRSCs from hESCs Using Small Molecules.

During the early stages of vertebrate embryonic development, eye field specification is induced under the influence of Wnt and BMP signaling gradients[16,17]. Previous studies indicate that the gradient of Wnt signaling is important in establishing forebrain and midbrain identities during early development. Downregulation of Wnt signaling leads to formation of the forebrain, where the eye field resides. Accordingly, treating hESC-derived embryoid bodies with Dkk1, a potent Wnt inhibitor, and noggin, a BMP antagonist, promotes the development of an eye field[3,19]. In addition, under dual SMAD inhibition by exposure to SB431542 (a selective and potent inhibitor of the transforming growth factor-beta (TGF-β) superfamily type I activin receptor-like kinases ALK-4, -5, and -7) and LDN193189 (a selective inhibitor of BMP type I receptors ALK-2 and ALK-3, a noggin analog), hESCs are likely to become forebrain/eye field precursors that strongly express PAX6 and LHX2[20,21]. Therefore, we developed a chemically defined culture protocol to induce the differentiation of hESCs toward hpRSCs under synergistic inhibition of Wnt and TGF-β/BMP signaling activities using the small molecule inhibitors IWP2 (Inhibitor of Wnt Production-2, a Dkk1 analog)[22], LDN193189, and SB431542 (referred to hereafter as IWP, LDN, and SB, respectively). The pluripotent hESCs were plated on Matrigel-coated plates and cultured under feeder-free and serum-free conditions to near-confluence. Subsequently, the culture was switched to hpRSC priming medium supplemented with the IWP-LDN-SB small molecule cocktail for one week. Under this treatment, the majority of hESCs were converted into tightly packed cells. The massive induction of hpRSCs was confirmed by immunocytochemical labeling of key early eye field transcription factors[3,23]. Over 90% of cells were positive for both PAX6 and LHX2, two key transcription factors expressed by eye field progenitors (FIG. 1b). Most hESC-derived hpRSCs also expressed nestin, a typical marker of primitive neuroepithelial stem cells (FIG. 1c). In addition, the hESC-derived hpRSCs retained proliferative activity as evidenced by strong expression of Ki67 (FIG. 1c). The induction of hpRSCs was further confirmed by real-time PCR to assess the expression of typical early eye field transcription factor genes including PAX6, RX, LHX2, SIX3, and SIX6. We found over 20- to 1200-fold increased expression of these retinal progenitor markers in hpRSCs after six days of induction (FIG. 1d). The expression levels of these genes were maintained over at least two passages in culture.

Transcriptional Profile of hpRSCs.

Figure 2:
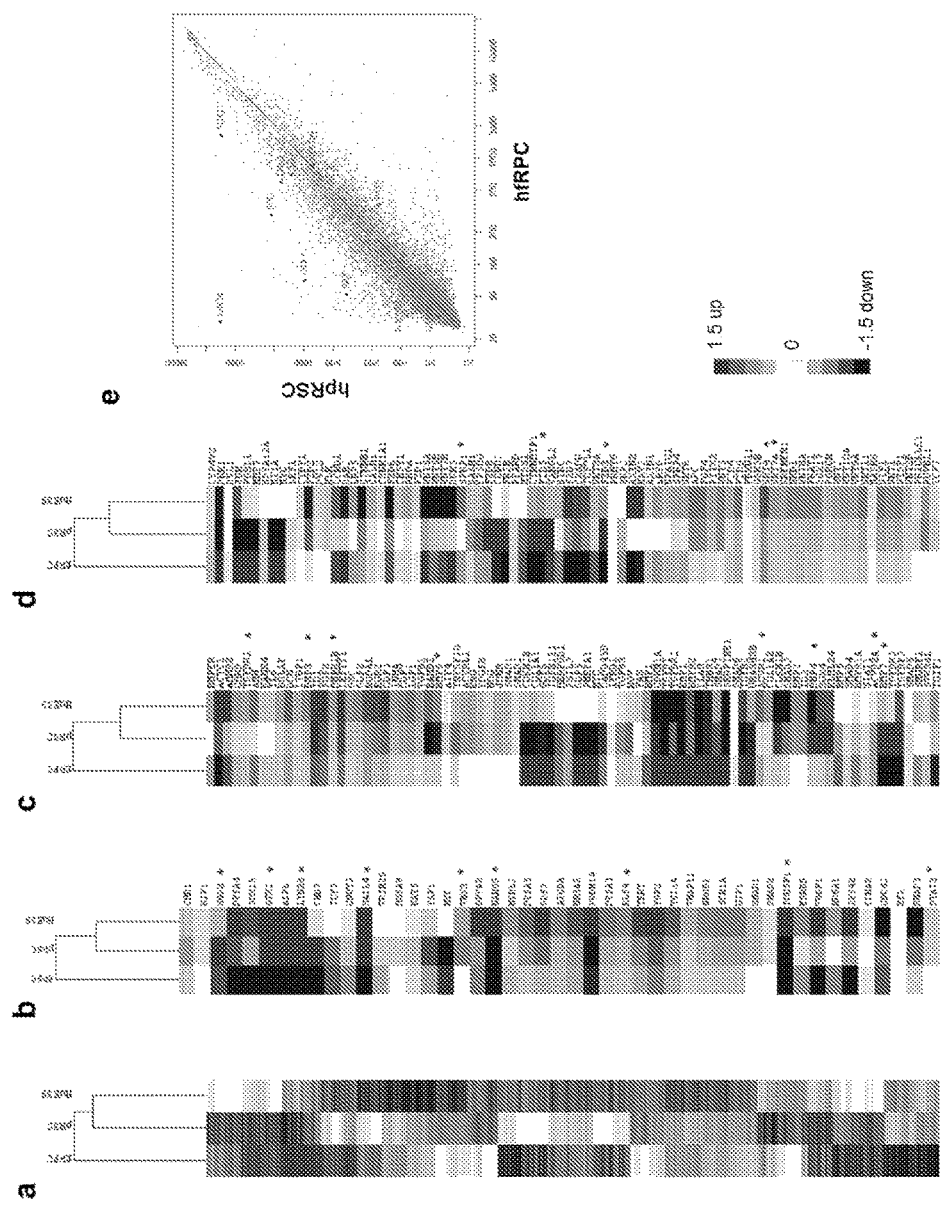
FIG. 2. Transcriptome analysis of hESC-derived hpRSCs. Heat maps of expression for genes differentially regulated in hfRPCs, hpRSCs, and the hESC line HuES9. Unsupervised clustering of cell types shows the transitional status of hESC-derived hpRSCs between hfRPCs and the parental hESC line HuES9. (a) Genome-wide transcriptome analysis. (b) Pluripotency regulation. (c) TGF-β superfamily signaling pathway. (d) Wnt signaling pathway. Red, high expression; blue, low expression relative to the other two cell types. (e) Pair-wise scatter plot analysis between hpRSCs and hfRPCs. Signal intensities are shown for transcripts in hfRPCs versus hpRSCs. The diagonal line indicates equal expression levels in genes between the two cell types. Genes marked with * are important for hpRSC stemness and specification.

In order to gain a global view of hpRSC identity and investigate its molecular signature relative to its parental cell, the undifferentiated hESC, and more committed retinal progenitor cells, we compared the hpRSC transcriptome to those of hESCs and human 17-week fetal retinal progenitor cells (hfRPCs) by microarray. The data indicated that hpRSCs are in a transitional state within the differentiation process from pluripotent hESCs to the neural retinal fate-restricted hfRPCs (FIG. 2a). Significant downregulation of key hESC pluripotency transcription factors, such as POU5F1 (OCT4), NANOG, KLF4, and TBX3, was observed in hpRSCs. Interestingly, LIN28 and SALL4, two transcription factors that define stemness in embryonic stem cells as well as several tissue lineages[24-26], were expressed at similar levels in hpRSCs as in hESCs, but at significantly reduced levels in hfRPCs (FIG. 2b, e). Moreover, elevated SOX2 expression was detected only in hpRSCs (FIG. 2b), indicating the primitive neuroectodermal state of hpRSCs[27]. Accordant with the known molecular signature associated with eye field formation[23], hpRSCs displayed decreased expression of some genes in the TGF-β superfamily, such as SMAD1, SMAD2, TGF/β3, BMP3, BMP6, TGFBR1, and BMPR1B (FIG. 2c). Notably, BMP4 and BMP7, which are sufficient and essential for RPE development in vivo[28], had higher expression levels in hpRSCs than in hfRPCs. Consistent with previous studies[17,29], expression of WNT4 and WNT11, which are normally suppressed in the eye field but elevated beyond the posterior boundary, were decreased in hpRSCs (FIG. 2d). Similarly, SRFP1 (an endogenous Wnt inhibitor) and FZD3/5 (receptors for Wnt signaling proteins), which are known to be important in eye field formation[30], were expressed strongly in hpRSCs (FIG. 2d). Furthermore, pair-wise comparison analysis of hpRSC and hfRPC transcriptomes affirmed the transitional state of hpRSCs during eye field specification. A set of typical early eye field transcription factor genes including OTX2, RAX LHX2, SIX3, and SIX6, were all expressed more prominently in hpRSCs than in hfRPCs with the exception of PAX6, which stays active throughout retinogenesis (FIG. 2e). Downregulation of members of the FGF signaling pathway was also observed, including FGFR1/2/3 and FGF3/8 (FIG. 7a) that are known for promoting retinal neurogenesis[31], suggesting that hpRSCs have not yet committed to becoming RPE or neural retina. The data demonstrate that the derivation of hpRSCs from hESCs may recapitulate eye field specification and that hpRSCs are poised to enter retinal sublineage differentiation.

Directed Differentiation of Retinal Ganglion Cells from hESC-Derived hpRSCs.

Figure 3:
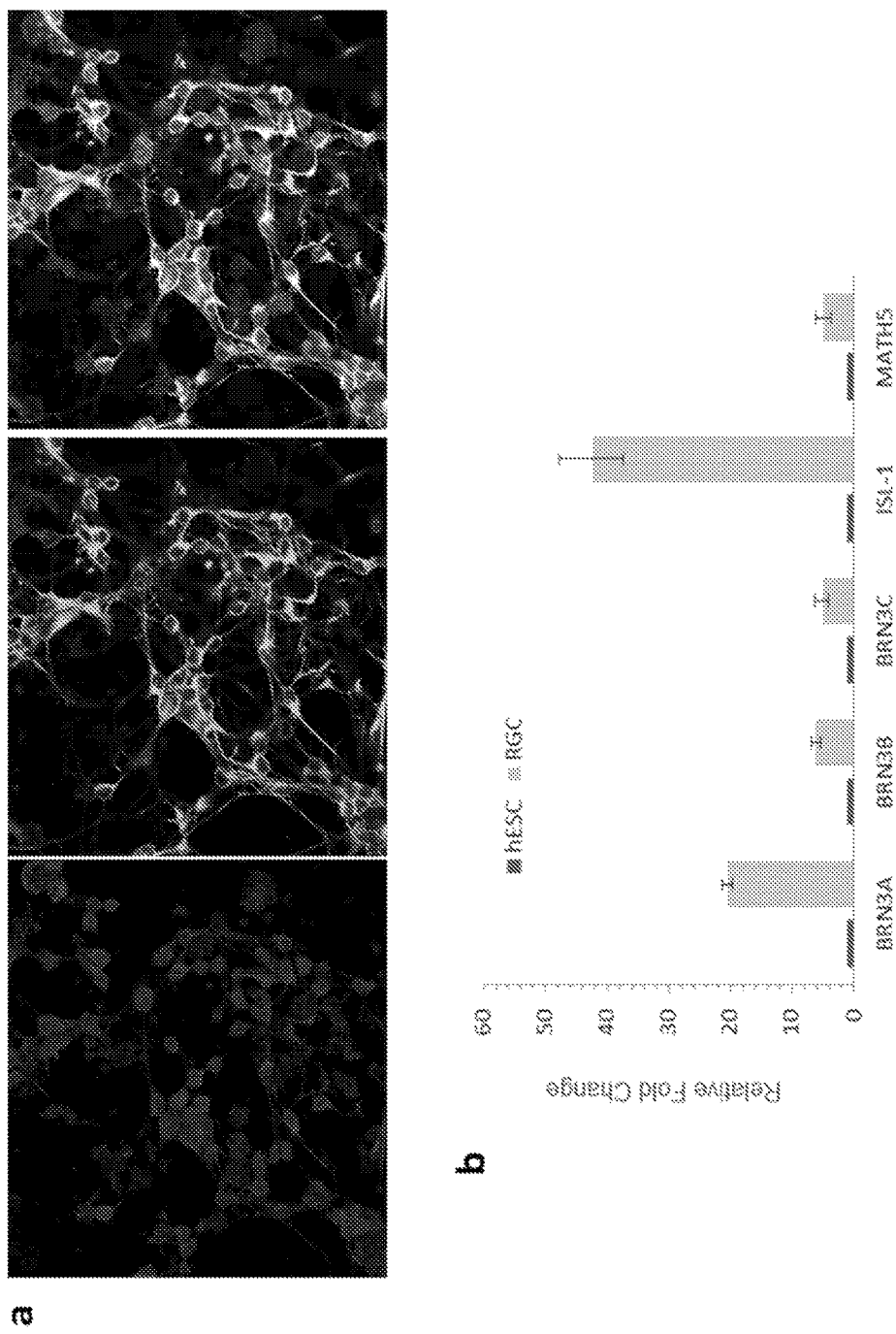
FIG. 3. hpRSCs can be specified to the fate of retinal ganglion cells (RGCs) under chemically defined culture conditions. (a) hpRSCs can differentiate into RGCs with high efficiency. After two weeks of culture under conditions for RGC induction, differentiated cells displayed long neuronal processes and expressed typical RGC markers such as BRN3 (red) and TUJ1 (green). Cell nuclei were counterstained with Hoechst 33342 (blue). (b) Real-time qPCR analysis for expression of RGC-specific transcription factors in cells differentiated from hpRSCs.
Figure 7:
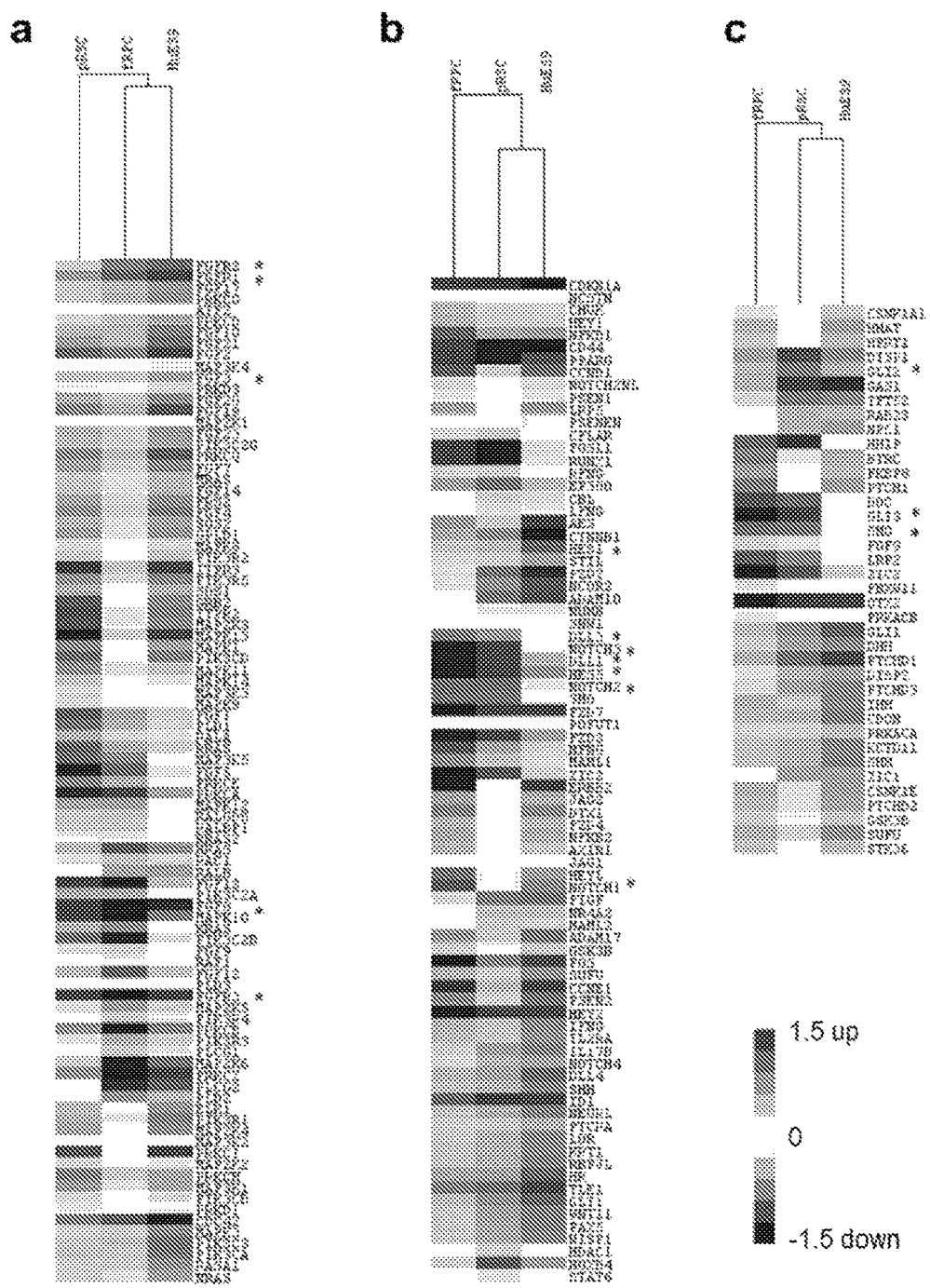
FIG. 7. Representative heat maps of expression for genes involved in FGF (a), Notch (b), and Hedgehog signaling pathways (c) in hfRPCs, HuES9, and HuES9-derived hpRSCs. Genes labeled with * are known to be important in retinogenesis.

To investigate whether hESC-derived hpRSCs have the potential to generate different retinal sublineage cell types in culture, we took a small molecule-based approach to mimicking inductive cues of early eye development. We directed the differentiation of hpRSCs toward specific retinal cell fates in vitro. Retinal ganglion cells (RGCs) are a major type of retinal neuron and play a critical role in transmitting visual signals from the retina to several regions of the brain. We first tested whether hESC-derived hpRSCs could be instructed to differentiate into RGCs under chemically defined conditions. Previous results demonstrated that inhibition of Notch and VEGFR signaling is important for RGC specification[32,33]. Our transcription profiling analysis indicated that expression of several members of the Notch and VEGFR signaling pathways, such as NOTCH1, NOTCH2, NOTCH3, DLL1, DLL3, HESS, and HES1, were significantly upregulated in hpRSCs (FIG. 7b). We therefore formulated a cocktail of small molecule inhibitors including IWP2, DAPT, and PD173074 that could inhibit the activities of Wnt, Notch, and VEGFR signaling, respectively. The treatment rapidly committed hpRSCs to an RGC fate. After two weeks of induction in the presence of these three small molecule inhibitors, the majority of cells were positive for both TUJ1 and BRN3, markers of RGCs (FIG. 3a). Quantitative PCR analysis showed remarkable upregulation of RGC precursor-specific transcription factor genes, such as BRN3A, BRN3B, ISL-1, and MATH5, after the first six days of induction (FIG. 3b).

Directed Differentiation of Photoreceptors from hESC-Derived hpRSCs.

Figure 4:
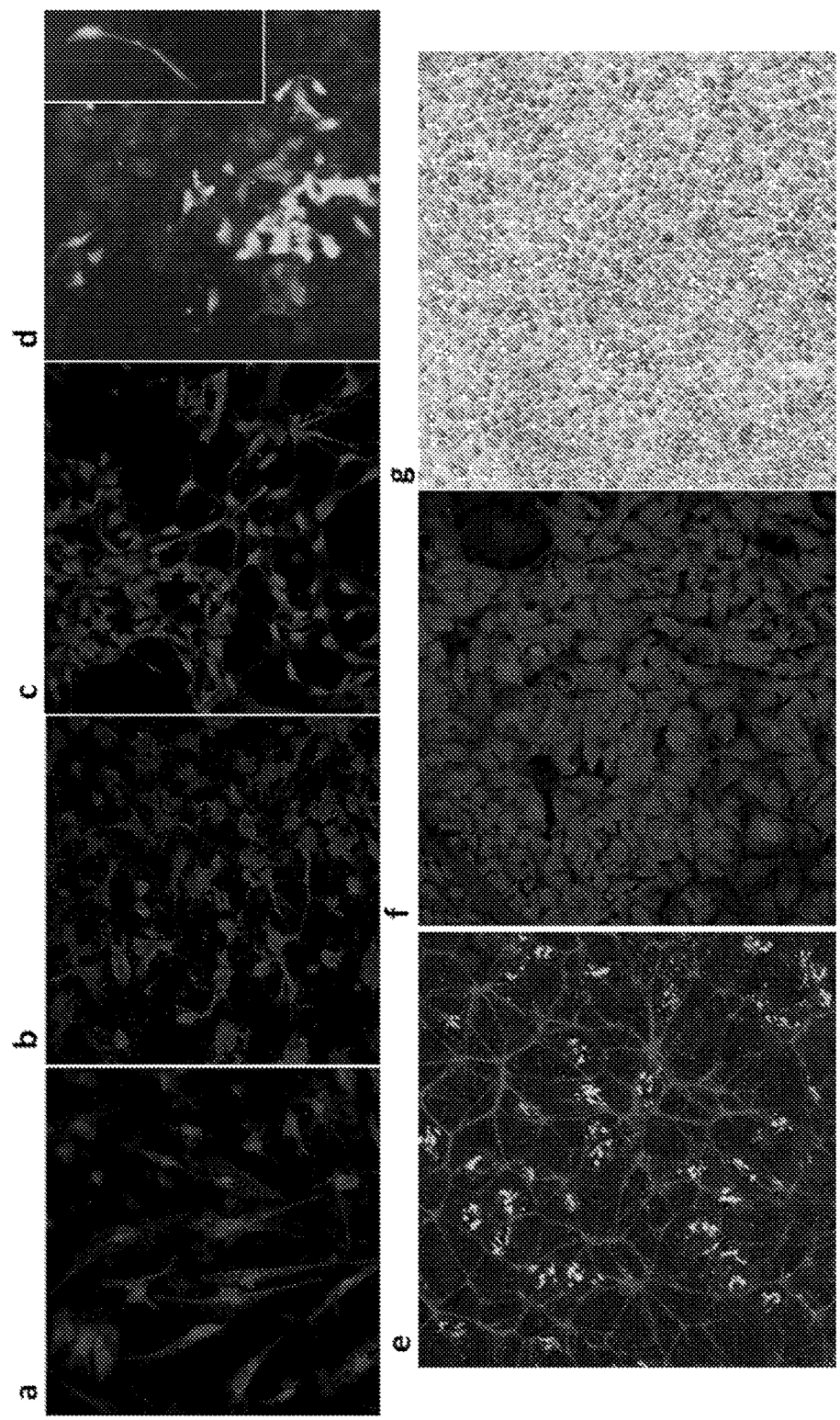
FIG. 4. Characterization of hpRSC differentiation to either neuronal or non-neuronal retinal cell fates under defined culture conditions. (a-d) Photoreceptor induction as evidenced by immunocytochemical detection of recoverin (a), blue opsin (OPN1SW) (b), and rhodopsin (c), as well as the expression of the photoreceptor-specific reporter IRBP-GFP (d); a well-differentiated photoreceptor showed the typical morphology with a long outer process and short inner process (d, inset). (e-g) RPE induction; (e) RPE formation as demonstrated by the early expression of RPE65 (green) and phalloidin staining the polygonal shape of RPE cells (red); (f) elevated RPE65 expression observed after three weeks in culture (red); (g) pigmented RPE appeared after prolonged maturation in culture. (a-f) Cell nuclei were counterstained with Hoechst 33342 (blue).

Photoreceptors are a major cell type in the retina and are responsible for the initiation of visual signal transduction. hpRSCs expressed several hedgehog (HH) signaling genes, such as GLI2, GLI3, and smoothened (SMO) (FIG. 7c), at higher levels than did hESCs and hfRPCS, suggesting that hpRSCs were inclined to differentiate toward photoreceptors. We therefore developed a modified in vitro photoreceptor differentiation method based on previous studies[7] and utilized small molecules to direct the differentiation process. The restriction of photoreceptor fate from hpRSCs has been achieved with a two-step process[7]. During the initial phase, hpRSCs were treated with the small molecule inhibitors SB, CHIR99021, DAPT, and IWP2 to suppress ALK4/5/7, GSK-3, Notch, and Wnt signaling activities, respectively, and with purmorphamine, a small molecule activator of the Shh signaling pathway[34]. Robust cell growth and proliferation, but not expression of photoreceptor-specific markers, were observed during this initial phase as previously described[35]. During the second phase, the culture was shifted to medium supplemented with retinoic acid and taurine as described in a previous report[7], which induced morphological changes including extension of cellular processes in some cells after one week. To identify the fate of these differentiated cells, we examined the expression of photoreceptor-specific markers by immunocytochemistry. By day 14 after the initial induction, the pan-photoreceptor marker recoverin (FIG. 4a), cone cell-specific marker OPN1SW or blue opsin (FIG. 4b), and rod cell-specific marker rhodopsin (FIG. 4c) were detected. To determine whether photoreceptors differentiated from hpRSCs in vitro also express human interphotoreceptor retinoid binding protein (IRBP), a marker of both rod and cone photoreceptors[36], we infected hpRSCs with an IRBP-GFP lentivirus and differentiated the transduced cells toward the photoreceptor fate. This approach has been shown to specifically mark photoreceptors in transgenic mice and in human, mouse, and chick retinal explants[37,38]. After 12 days of differentiation, GFP-positive cells started to appear. By day 16, clusters of GFP-expressing photoreceptors were clearly visible (FIG. 4d). After further maturation, hpRSC-derived photoreceptors displayed typical morphological features such as a short inner process and long extended outer process, similar to an outer segment (FIG. 4d, inset).

Directed Differentiation of RPE from hpRSCs.

The RPE, a monolayer of cells between the neural retina and choriocapillaris, is the first committed retinal cell type to appear in the outer layer of the early optic cup[28]. To test whether hESC-derived hpRSCs are not only capable of differentiating into neuroretinal cells, but also non-neuronal RPE cells, we withdrew small molecule inhibitors from the adherent monolayer culture of hpRSCs and shifted to RPE initiation medium as previously described[39]. The removal of SMAD signaling inhibition and addition of activin A are important for directing hpRSCs toward the RPE fate, since activin A and BMP activities are required for RPE specification[28,39,40]. After RPE differentiation for 12 days, low expression levels of RPE65, an RPE-specific isomerase required for the conversion of all-trans retinol to 11-cis retinal and visual pigment regeneration, and the formation of polygonal actin bundles were observed inside of epithelium-like cells (FIG. 4e). Increased expression of RPE65 (FIG. 4f) and pigmentation of RPE (FIG. 4g) appeared after further maturation in culture.

Transplantation of hpRSCs.

Figure 5:
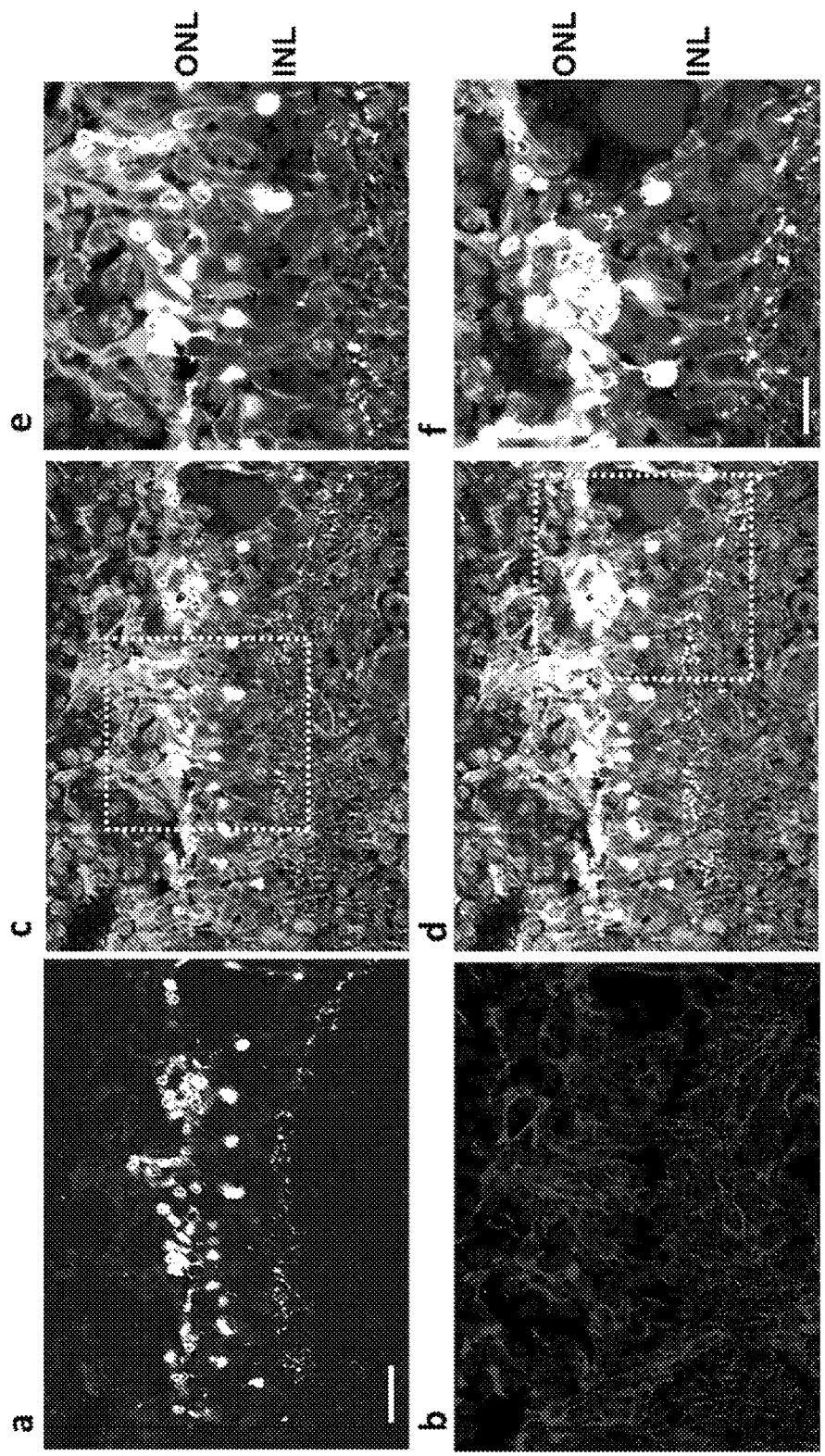
FIG. 5. In vivo integration and differentiation of grafted hpRSCs in neonatal nude rats. Confocal images of immunohistochemically stained cryosections of retina after transplantation with hpRSCs. Significant integration of grafted GFP (green)-expressing human cells was observed in recipient neural retina. Some GFP-expressing cells co-localized with recoverin (white)-positive cells (a, c, e); immunostaining of retinal progenitor marker nestin (red) was detected in many grafted GFP-expressing cells (b, d, f). Cell nuclei were counterstained with Hoechst 33342 (blue). Scale bars: a-d=30 μm; e-f=15 μm.
Figure 6:
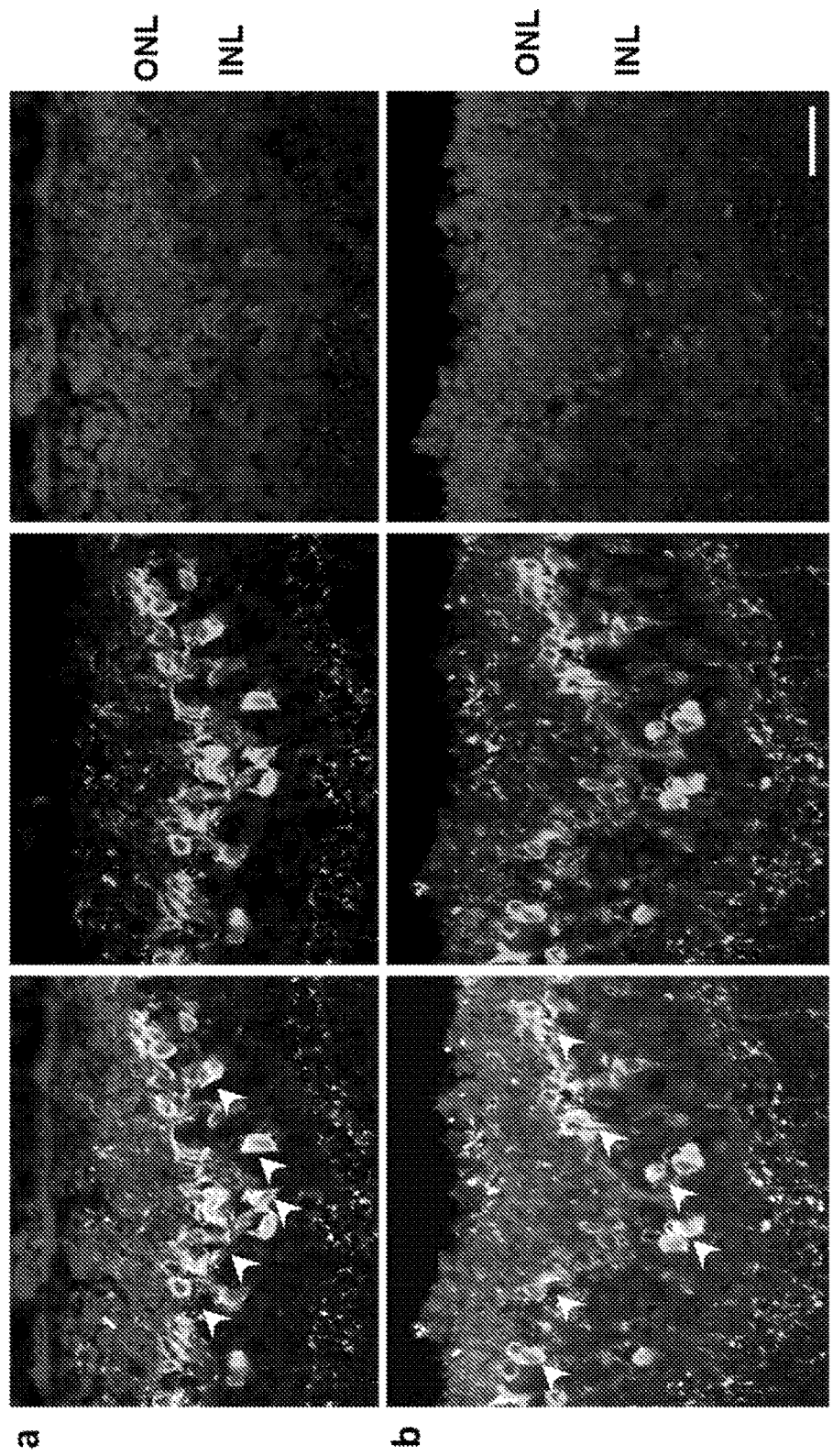
FIG. 6. Integration and differentiation of grafted hpRSCs in photoreceptor layers of RCS rats two months post-transplantation. (a) The grafted cells underwent immunocytochemical labeling with HSA antibodies (red). Some of the grafted cells adopted the fate of recoverin (green)-expressing photoreceptors (arrowheads). (b) hpRSC-derived cones (arrowheads) were positive for both red/green opsin (green) and HSA (red). Cell nuclei were counterstained with Hoechst 33342 (blue). Scale bar=20 μm.
Figure 8:
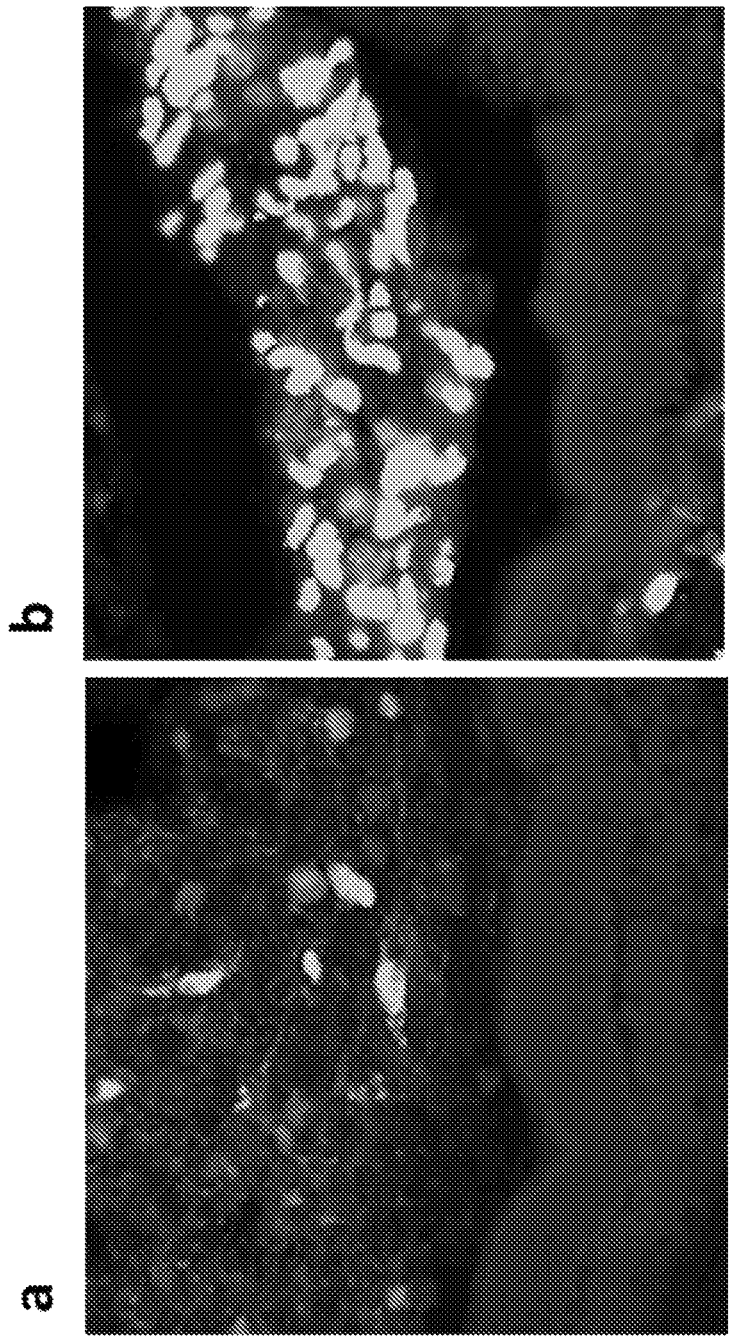
FIG. 8. In vivo transplantation of hpRSCs in the absence (a) or presence (b) of HAMC hydrogel in nude rats at P21. Retinal sections were processed at six weeks post-transplantation. In the absence of hydrogel, fewer hpRSCs survived and were often surrounded by scar tissue in the subretinal space. In the presence of HAMC hydrogel, transplanted hpRSCs were spread across the subretinal space and in the neural retinal layers. Grafted hpRSCs were labeled with human nuclear antigen staining (green). Cell nuclei were counterstained with Hoechst 33342 (blue).

We next determined the ability of hESC-derived hpRSCs to survive and differentiate into photoreceptors after being grafted into the subretinal space of rodent eyes. To avoid immune rejection of human cells, we used athymic nude rats for transplantation. Six weeks after transplantation with ~50,000 hpRSCs, grafted human cells were observed in the subretinal tissue of recipient eyes, but the number of human specific antigen (HSA)-positive cells was often limited and surrounded by scar tissue (FIG. 8a). In order to overcome the tendency of cells to aggregate and to increase cell survival rate after subretinal transplantation, we chose to deliver cells in a hydrogel composed of hyaluronic acid and methylcellulose (HAMC) instead of saline. Recently, it has been demonstrated that transplantation of murine eye-derived retinal progenitor cells with HAMC hydrogel can improve the survival, distribution, and differentiation of grafted cells[41,42]. We injected hpRSCs mixed with HAMC (0.5/0.5% w/w) hydrogel into the subretinal space of nude rats. At six weeks post-transplantation, increased numbers of grafted human cells survived and were distributed broadly across the subretinal area (FIG. 8b). Thus, for subsequent transplantation experiments, we delivered hpRSCs in HAMC hydrogel unless indicated otherwise. Since the neural retina is still developing in neonatal animals, it may provide a permissible environment for the integration and differentiation of transplanted hpRSCs. To test this hypothesis, we injected GFP-tagged hpRSCs into the subretinal space of neonatal nude rats and observed significant integration of GFP-expressing hpRSCs in the neural retina, including the outer nuclear layer (ONL) and the inner nuclear layer (INL) six days post-transplantation (FIG. 5). Some of the GFP-positive cells that integrated into the ONL co-localized with the typical photoreceptor marker recoverin (FIG. 5a, e, f). Notably, many grafted GFP-positive cells continued to express nestin (FIG. 5b, d, f), a marker of uncommitted hpRSCs, indicating that these cells were not yet committed to a particular retinal cell fate. Next, we tested whether hpRSCs have the ability to differentiate into a desirable cell type such as photoreceptors in an animal model of retinal degeneration, the Royal College of Surgeons (RCS) rat. The RCS rat harbors a mutation in the Mer receptor tyrosine kinase, which causes photoreceptor degeneration via defective RPE phagocytosis[43,44]. We injected hpRSCs into the subretinal space of RCS rats at postnatal day 21 (P21) and examined differentiation and integration after two months. Cryosections of transplanted eyes were co-immunostained with antibodies against HSA and a photoreceptor marker, either recoverin (FIG. 6a) or red/green opsin (FIG. 6b). Layers of grafted human cells were detected in the area adjacent to the ONL. Many recoverin-positive and red/green opsin-positive cells were also positive for HSA (FIG. 6). The presence of double-positively labeled cells indicated that some grafted hpRSCs commit to the photoreceptor fate in degenerating retinas.

Discussion

Here we have used a small molecule-based approach to recapitulate the process of in vivo retinal development from undifferentiated hESCs and produced hpRSCs under chemically defined culture conditions. hESC-derived hpRSCs exhibited the typical features of neuroepithelial cells of the eye field. Induction was achieved in a rapid and efficient manner by the synergistic inhibition of Nodal, BMP, and Wnt signaling in undifferentiated hESCs. hESC-derived hpRSCs proliferated and actively expressed typical early eye field transcription factors (i.e. PAX6, LHX2, RAX, OTX2, and SIX3) as well as stemness factors (i.e. SOX2, LIN28, SALL4, and STAT3). When provided with specific differentiation cues, these primitive retinal stem cells could be directed to commit to either a neuronal fate, such as RGCs or photoreceptors, or non-neuronal RPE. Moreover, we demonstrated that transplanted hpRSCs were able to integrate, survive, and differentiate into desired cell types in vivo. Encouragingly, some grafted hpRSCs apparently differentiated into photoreceptors in the remaining ONL two months post-transplantation in RCS rats, a model of retinal degeneration in which photoreceptors are lost beginning at P14 and are completely gone by the time the rats are three months old. Furthermore, we did not observe any tumor formation from grafted hpRSCs in the transplanted animals we have examined so far. Our results suggest that it is feasible to induce and expand hpRSCs in vitro in a scaled-up fashion suitable for clinical trials. In addition, this small molecule-based method could be used to generate patient iPSC-derived hpRSCs as well as more differentiated retinal progenitors or retinal neurons, which will have significant implications for "disease in a dish" modeling to investigate the molecular and cellular events that underlie the pathogenesis of retinal degeneration.

REFERENCES

1 Seiler, M. J. & Aramant, R. B. Cell replacement and visual restoration by retinal sheet transplants. *Prog Retin Eye Res* 31, 661-687, doi:10.1016/j.preteyeres.2012.06.003 (2012).

2 Banin, E. et al. Retinal incorporation and differentiation of neural precursors derived from human embryonic stem cells. *Stem Cells* 24, 246-257 (2006).

3 Lamba, D. A., Karl, M. O., Ware, C. B. & Reh, T. A. Efficient generation of retinal progenitor cells from human embryonic stem cells. *Proc Natl Acad Sci USA* 103, 12769-12774 (2006).

4 Klimanskaya, I. et al. Derivation and comparative assessment of retinal pigment epithelium from human embryonic stem cells using transcriptomics. *Cloning Stem Cells* 6, 217-245, doi:10.1089/clo.2004.6.217 (2004).

5 Vugler, A. et al. Elucidating the phenomenon of HESC-derived RPE: anatomy of cell genesis, expansion and retinal transplantation. *Exp Neurol* 214, 347-361, doi: 10.1016/j.expneurol.2008.09.007 (2008).

6. Ukrohne, T. U. et al. Generation of retinal pigment epithelial cells from small molecules and OCT4 reprogrammed human induced pluripotent stem cells. *Stem cells translational medicine* 1, 96-109, doi:10.5966/sctm.2011-0057 (2012).

7. Osakada, F. et al. Toward the generation of rod and cone photoreceptors from mouse, monkey and human embryonic stem cells. *Nat Biotechnol* 26, 215-224 (2008).

8. Gonzalez-Cordero, A. et al. Photoreceptor precursors derived from three-dimensional embryonic stem cell cultures integrate and mature within adult degenerate retina. *Nat Biotechnol*, doi:10.1038/nbt.2643 (2013).

9. Lamba, D. A. et al. Generation, Purification and Transplantation of Photoreceptors Derived from Human Induced Pluripotent Stem Cells. *PLoS ONE* 5, e8763, doi:10.1371/journal.pone.0008763 (2010).

10. Schwartz, S. D. et al. Embryonic stem cell trials for macular degeneration: a preliminary report. *Lancet* 379, 713-720, doi:10.1016/S0140-6736(12)60028-2 (2012).

11. Adelmann, H. B. The problem of cyclopia—Part I. *Q Rev Biol* 11, 161-182, doi:Doi 10.1086/394504 (1936).

12. Li, H., Tierney, C., Wen, L., Wu, J. Y. & Rao, Y. A single morphogenetic field gives rise to two retina primordia under the influence of the prechordal plate. *Development* 124, 603-615 (1997).

13. Nakano, T. et al. Self-Formation of Optic Cups and Storable Stratified Neural Retina from Human ESCs. *Cell Stem Cell* 10, 771-785, doi:10.1016/j.stem.2012.05.009 (2012).

14. Eiraku, M. et al. Self-organizing optic-cup morphogenesis in three-dimensional culture. *Nature* 472, 51-56, doi:10.1038/nature09941 (2011).

15. Meyer, J. S. et al. Modeling early retinal development with human embryonic and induced pluripotent stem cells. *Proc Natl Acad Sci USA* 106, 16698-16703, doi: 10.1073/pnas.0905245106 (2009).

16. del Barco Barrantes, I., Davidson, G., Grone, H. J., Westphal, H. & Niehrs, C. Dkk1 and noggin cooperate in mammalian head induction. *Genes Dev* 17, 2239-2244, doi:10.1101/gad.269103 (2003).

17. Cavodeassi, F. et al. Early stages of zebrafish eye formation require the coordinated activity of Wnt11, Fz5, and the Wnt/beta-catenin pathway. *Neuron* 47, 43-56, doi:10.1016/j.neuron.2005.05.026 (2005).

18. Li, W. et al. Rapid induction and long-term self-renewal of primitive neural precursors from human embryonic stem cells by small molecule inhibitors. *Proceedings of the National Academy of Sciences* 108, 8299-8304, doi: 10.1073/pnas.1014041108 (2011).

19. Reh, T. A., Lamba, D. & Gust, J. Directing human embryonic stem cells to a retinal fate. *Methods in molecular biology* 636, 139-153, doi:10.1007/978-1-60761-691-7_9 (2010).

20. Chambers, S. M. et al. Highly efficient neural conversion of human ES and iPS cells by dual inhibition of SMAD signaling. *Nat Biotechnol* 27, 275-280, doi:10.1038/nbt.1529 (2009).

21. Kriks, S. et al. Dopamine neurons derived from human ES cells efficiently engraft in animal models of Parkinson's disease. *Nature* 480, 547-551, doi:10.1038/nature10648 (2011).

22. Chen, B. et al. Small molecule-mediated disruption of Wnt-dependent signaling in tissue regeneration and cancer. *Nature chemical biology* 5, 100-107, doi:10.1038/nchembio.137 (2009).

23. Zuber, M. E., Gestri, G., Viczian, A. S., Barsacchi, G. & Harris, W. A. Specification of the vertebrate eye by a network of eye field transcription factors. *Development* 130, 5155-5167, doi:10.1242/dev.00723 (2003).

24. Shyh-Chang, N. & Daley, G. Q. Lin28: primal regulator of growth and metabolism in stem cells. *Cell Stem Cell* 12, 395-406, doi:10.1016/j.stem.2013.03.005 (2013).

25. Yang, J. et al. Enhanced self-renewal of hematopoietic stem/progenitor cells mediated by the stem cell gene Sall4. *Journal of hematology & oncology* 4, 38, doi: 10.1186/1756-8722-4-38 (2011).

26. Aguila, J. R. et al. SALL4 is a robust stimulator for the expansion of hematopoietic stem cells. *Blood* 118, 576-585, doi:10.1182/blood-2011-01-333641 (2011).

27. Graham, V., Khudyakov, J., Ellis, P. & Pevny, L. SOX2 functions to maintain neural progenitor identity. *Neuron* 39, 749-765 (2003).

28. Muller, F., Rohrer, H. & Vogel-Hopker, A. Bone morphogenetic proteins specify the retinal pigment epithelium in the chick embryo. *Development* 134, 3483-3493, doi:10.1242/dev.02884 (2007).

29. Maurus, D., Heligon, C., Burger-Schwarzler, A., Brandli, A. W. & Kuhl, M. Noncanonical Wnt-4 signaling and EAF2 are required for eye development in Xenopus laevis. *The EMBO journal* 24, 1181-1191, doi:10.1038/sj.emboj.7600603 (2005).

30. Esteve, P., Lopez-Rios, J. & Bovolenta, P. SFRP1 is required for the proper establishment of the eye field in the medaka fish. *Mech Dev* 121, 687-701, doi:10.1016/j.mod.2004.03.003 (2004).

31. Martinez-Morales, J. R. et al. Differentiation of the vertebrate retina is coordinated by an FGF signaling center. *Dev Cell* 8, 565-574, doi:10.1016/j.devcel.2005.01.022 (2005).

32. Austin, C. P., Feldman, D. E., Ida, J. A., Jr. & Cepko, C. L. Vertebrate retinal ganglion cells are selected from competent progenitors by the action of Notch. *Development* 121, 3637-3650 (1995).

33. Hashimoto, T., Zhang, X. M., Chen, B. Y. & Yang, X. J. VEGF activates divergent intracellular signaling components to regulate retinal progenitor cell proliferation and neuronal differentiation. *Development* 133, 2201-2210, doi:10.1242/dev.02385 (2006).

34. Sinha, S. & Chen, J. K. Purmorphamine activates the Hedgehog pathway by targeting Smoothened. *Nature chemical biology* 2, 29-30, doi:10.1038/nchembio753 (2006).

35. Czekaj, M. et al. In vitro expanded stem cells from the developing retina fail to generate photoreceptors but differentiate into myelinating oligodendrocytes. *PLoS ONE* 7, e41798, doi:10.1371/journal.pone.0041798 (2012).

36. Eisenfeld, A. J., Bunt-Milam, A. H. & Saari, J. C. Immunocytochemical localization of interphotoreceptor retinoid-binding protein in developing normal and RCS rat retinas. *Invest Ophthalmol Vis Sci* 26, 775-778 (1985).

37. Yokoyama, T., Liou, G. I., Caldwell, R. B. & Overbeek, P. A. Photoreceptor-specific activity of the human interphotoreceptor retinoid-binding protein (IRBP) promoter in transgenic mice. *Exp Eye Res* 55, 225-233 (1992).

38. Lamba, D. A. et al. Generation, purification and transplantation of photoreceptors derived from human induced pluripotent stem cells. *PLoS ONE* 5, e8763, doi:10.1371/journal.pone.0008763 (2010).

39. Idelson, M. et al. Directed differentiation of human embryonic stem cells into functional retinal pigment epithelium cells. *Cell Stem Cell* 5, 396-408, doi:10.1016/j.stem.2009.07.002 (2009).

40 Fuhrmann, S., Levine, E. M. & Reh, T. A. Extraocular mesenchyme patterns the optic vesicle during early eye development in the embryonic chick. *Development* 127, 4599-4609 (2000).
41 Ballios, B. G., Cooke, M. J., van der Kooy, D. & Shoichet, M. S. A hydrogel-based stem cell delivery system to treat retinal degenerative diseases. *Biomaterials* 31, 2555-2564, doi:10.1016/j.biomaterials.2009.12.004 (2010).
42 Liu, Y. et al. The application of hyaluronic acid hydrogels to retinal progenitor cell transplantation. *Tissue engineering. Part A* 19, 135-142, doi:10.1089/ten.TEA.2012.0209 (2013).
43 Edwards, R. B. & Szamier, R. B. Defective phagocytosis of isolated rod outer segments by RCS rat retinal pigment epithelium in culture. *Science* 197, 1001-1003 (1977).
44 D'Cruz, P. M. et al. Mutation of the receptor tyrosine kinase gene Mertk in the retinal dystrophic RCS rat. *Hum Mol Genet* 9, 645-651 (2000).
45 Schmitt, S. et al. Molecular characterization of human retinal progenitor cells. *Invest Ophthalmol Vis Sci* 50, 5901-5908, doi:10.1167/iovs.08-3067 (2009).
46 Maminishkis, A. et al. Confluent monolayers of cultured human fetal retinal pigment epithelium exhibit morphology and physiology of native tissue. *Invest Ophthalmol Vis Sci* 47, 3612-3624, doi:10.1167/iovs.05-1622 (2006).
47 Edgar, R., Domrachev, M. & Lash, A. E. Gene Expression Omnibus: NCBI gene expression and hybridization array data repository. *Nucleic Acids Res* 30, 207-210 (2002).
48 Kurian, L. et al. Conversion of human fibroblasts to angioblast-like progenitor cells. *Nature methods* 10, 77-83, doi:10.1038/nmeth.2255 (2013).
49 de Hoon, M. J., Imoto, S., Nolan, J. & Miyano, S. Open source clustering software. *Bioinformatics* 20, 1453-1454, doi:10.1093/bioinformatics/bth078 (2004).
50 Garamszegi, N., Garamszegi, S. P., Shehadeh, L. A. & Scully, S. P. Extracellular matrix-induced gene expression in human breast cancer cells. *Molecular cancer research: MCR* 7, 319-329, doi:10.1158/1541-7786.MCR-08-0227 (2009).
51 Burkhalter, R. J., Symowicz, J., Hudson, L. G., Gottardi, C. J. & Stack, M. S. Integrin regulation of beta-catenin signaling in ovarian carcinoma. *J Biol Chem* 286, 23467-23475, doi:10.1074/jbc.M110.199539 (2011).
52 Liefke, R. et al. Histone demethylase KDM5A is an integral part of the core Notch-RBP-J repressor complex. *Genes Dev* 24, 590-601, doi:10.1101/gad.563210 (2010).
53 Przybyla, L. M. & Voldman, J. Attenuation of extrinsic signaling reveals the importance of matrix remodeling on maintenance of embryonic stem cell self-renewal. *Proc Natl Acad Sci USA* 109, 835-840, doi:10.1073/pnas.1103100109 (2012).
54 Varjosalo, M. & Taipale, J. Hedgehog signaling. *J Cell Sci* 120, 3-6, doi:10.1242/jcs.03309 (2007).
55 Lu, B. et al. Neural stem cells derived by small molecules preserve vision. *Trans Vis Sci Tech* 2, 1-13, doi:10.1167/tvst.2.1.1 (2013).
56 Kang, C. E., Poon, P. C., Tator, C. H. & Shoichet, M. S. A new paradigm for local and sustained release of therapeutic molecules to the injured spinal cord for neuroprotection and tissue repair. *Tissue engineering. Part A* 15, 595-604, doi:10.1089/ten.tea.2007.0349 (2009).

What is claimed is:

1. An in vitro method for producing isolated mammalian primitive retinal stem cells (pRSCs) comprising:
    (a) culturing isolated pluripotent stem cells (PSCs) from a mammal on a solid support in N2B27 cell culture medium that is free of feeder cells, feeder-conditioned medium or serum so as to produce and grow an adherent culture of the isolated PSCs; and
    (b) contacting the adherent culture of the isolated PSCs so grown with a combination of an inhibitor of Wnt, an inhibitor of TGF-β, and an inhibitor of BMP signaling so as to differentiate the isolated PSCs of (b) into primitive retinal stem cells thereby producing isolated mammalian pRSCs.

2. The method of claim 1, wherein in step (a) the culture so produced is grown to near confluency before step (b).

3. The method of claim 1, wherein the mammal is a human, monkey, bear, rat, mouse, mink, rabbit, guinea pig, pig, dog, cat, goat, sheep, horse or cow.

4. The method of claim 1, wherein the isolated mammalian primitive retinal stem cells (pRSCs) are positive for expression of PAX6, LHX2, RAX, OTX2, SIX3 and/or SIX6 typical early eye field transcription factors.

5. The method of claim 1, wherein the isolated mammalian primitive retinal stem cells (pRSCs) which are positive for expression of stemness factors SOX2, and STAT3.

6. The method of claim 1, further comprising the isolated mammalian primitive retinal stem cells which are positive for expression of Ki67.

7. The method of claim 1, wherein the inhibitor of Wnt signaling is a small molecule inhibitor selected from the group consisting of Inhibitor of Wnt Production-1 (IWP-1), Inhibitor of Wnt Production-2 (IWP2), JW55, JW74, okadaic acid, tautomycin, SB239063, SB203580, ADP-HPD, 2-[4-(4-fluorophenyl) piperazin-1-yl]-6-methylpyrimidin-4 (3H)-one, PJ34, cambinol, sulindac, 3289-8625, scaffold A for series of analogs designed to inhibit Dishevelled protein, scaffold B for series of analogs designed to inhibit Dishevelled protein, JO 1-017a, NSC668036, filipin, IC261, PF670462, Bosutinib, PHA665752, Imatinib, ICG-001, ethacrynic acid, ethacrynic acid derivative, PKF115-584, PNU-74654, PKF118-744, CGP049090, PKF118-310, ZTM000990, BC21, GDC-0941, Rp-8-Br-cAMP, LGK974, C59, Ant 1.4Br/Ant 1.4CI, niclosamide, apicularen, bafilomycin, XAV939, IWR1, pyrvinium, NSC668036, 2,4-diamino-quinazoline, quercetin, and PKF115-584, and combinations thereof.

8. The method of claim 1, wherein the inhibitor of Wnt signaling is IWP2 or a Dkk1 analog.

9. The method of claim 8, wherein the Dkk1 analog is N-(6-methyl-1,3-benzothiazol-2-yl)-2-[(4-oxo-3-phenyl-6, 7-dihydrothieno[3,2-d]pyrimidin-2-yl)sulfanyl]acetamide having a chemical formula of $C_{22}H_{18}N_4O_2S_3$ and a chemical structure of:

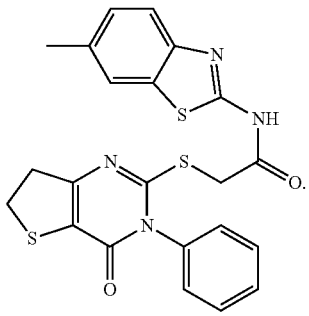 [SMILES: Cc1ccc2nc(NC(=O)CSc3nc4c(c(=O)n3-c3ccccc3)SCC4)sc2c1]

10. The method of claim 1, wherein the inhibitor of TGF-β signaling is a small molecule inhibitor selected from the group consisting of SB431542 (4-[4-(1,3-benzodioxol-5-yl)-5-(2-pyridinyl)-1H-imidazol-2-yl]benzamide), A 83-01 (3-(6-Methyl-2-pyridinyl)-N-phenyl-4-(4-quinolinyl)-1H-pyrazole-1-carbothioamide), SJN 2511 (2-(3-(6-Methylpyridine-2-yl)-1H-pyrazol-4-yl)-1,5-naphthyridine), D 4476 (4-[4-(2,3-Dihydro-1,4-benzodioxin-6-yl)-5-(2-pyridinyl)-1H-imidazol-2-yl]benzamide), LY 364947 (4-[3-(2-Pyridinyl)-1H-pyrazol-4-yl]-quinoline), SB 525334 (6-[2-(1,1-Dimethylethyl)-5-(6-methyl-2-pyridinyl)-1H-imidazol-4-yl]quinoxaline), SD 208 (2-(5-Chloro-2-fluorophenyl)-4-[(4-pyridyl)amino]pteridine); and wherein the inhibitor of BMP signaling is LDN-193189 (4-(6-(4-(piperazin-1-yl)phenyl)pyrazolo[1,5-a]pyrimidin-3-yl)quinoline).

11. The method of claim 1, wherein the inhibitor of TGF-β signaling is a small molecule inhibitor of the transforming growth factor-beta (TGF-β) superfamily type I activin receptor-like kinases ALK-4, -5, and -7.

12. The method of claim 11, wherein the small molecule inhibitor of the transforming growth factor-beta (TGF-β) superfamily type I activin receptor-like kinases ALK-4, -5, and -7 is SB431542 (CAS No. 301836-41-9) or 4-[4-(1,3-benzodioxol-5-yl)-5-(2-pyridinyl)-1H-imidazol-2-yl] benzamide having a chemical formula of $C_{22}H_{16}N_4O_3$ and a chemical structure of

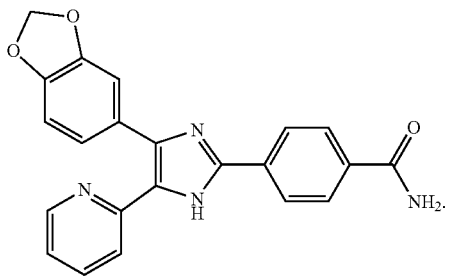 [SMILES: NC(=O)c1ccc(-c2nc(-c3ccc4c(c3)OCO4)c(-c3ccccn3)[nH]2)cc1]

13. The method of claim 1, wherein the inhibitor of BMP signaling is a small molecule inhibitor of BMP type I receptors ALK-2 and ALK-3 or a noggin analog.

14. The method of claim 13, wherein the small molecule inhibitor of BMP type I receptors ALK-2 and ALK-3 is 4-(6-(4-(piperazin-1-yl)phenyl)pyrazolo[1,5-a]pyrimidin-3-yl)quinoline having a chemical formula of $C_{25}H_{22}N_6$ and a chemical structure of

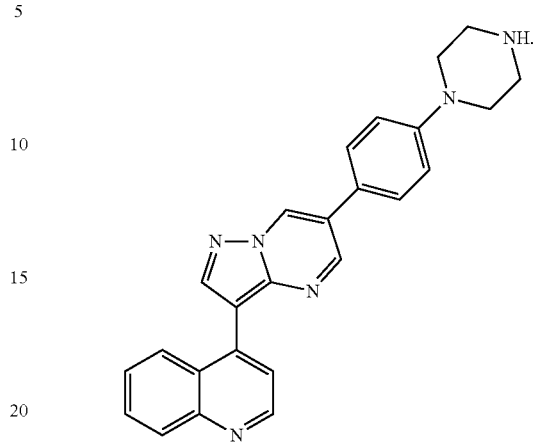

15. The method of claim 1, wherein the combination of the inhibitor for Wnt, the inhibitor of TGF-β and the inhibitor of BMP signaling is a combination of: (a) one or more inhibitors of Wnt Production-2 or Dkk1 analog; (b) one or more inhibitors of transforming growth factor-beta (TGF-β) superfamily type I activin receptor-like kinases ALK-4, -5, and -7; and (c) one or more inhibitors of BMP type I receptors ALK-2 and ALK-3 or a noggin analog, wherein the combination includes inhibitors for all three signaling pathways.

16. The method of claim 15, wherein the inhibitors are small molecules.

17. The method of claim 15, wherein the combination of inhibitors for Wnt, TGF-β and BMP signaling activities is a combination of IWP2 (CAS No. 686770-61-6), SB431542 (CAS No. 301836-41-9), and LDN-193189 (CAS No. 1062368-24-4) wherein the combination produces synergistic inhibition of Wnt and TGF-β and BMP signaling activities.

18. The method of claim 1, wherein the solid support or coated with reduced growth factor basement membrane.

19. A method for production of isolated human primitive retinal stem cells (hpRSCs) from isolated human pluripotent stem cells (hPSCs) comprising:
(a) culturing isolated hPSCs on a solid support with N2B27 culture medium in the absence of feeder cells, feeder-conditioned medium or serum for a sufficient time so as to grow nearly confluent, preferably to 80% cellular confluence;
(b) culturing the isolated hPSCs so grown on a solid support in a culture medium comprising basic FGF (bFGF) for a sufficient time so as to grow nearly confluent;
(c) culturing the isolated hPSCs of step b) on a solid support with a culture medium comprising a combination of small molecule inhibitors for Wnt, TGF-8 and BMP signaling so as to differentiate the isolated hPSCs to an isolated human primitive retinal stem cells, thereby, producing isolated hpRSCs.

20. The method of claim 19, wherein the combination of small molecule inhibitors for Wnt, TGF-β and BMP signaling activities in step (c) is (i) a combination of SB 431542, LDN193189 and IWP2, (ii) a combination of SB 431542, a noggin analog and IWP2, (iii) a combination of SB 431542, LDN193189 and a Dkk1 analog; or (iv) a combination of SB 431542, a noggin analog and a Dkk1 analog; wherein the combination of any of (i)-(iv) produces synergistic inhibition of Wnt and TGF-β and BMP signaling activities.

21. The in vitro method of claim 1, wherein the PSCs are selected from embryonic stem cells and induced pluripotent stem cells.

\* \* \* \* \*

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Beta-actin forward primer

<400> SEQUENCE: 1
gcgagaagat gacccagatc                                                   20

<210> SEQ ID NO 2
<211> LENGTH: 19
<212> TYPE: DNA
<213> ORGANISM: Artificial Sequence
<220> FEATURE:
<223> OTHER INFORMATION: Beta-actin reverse primer

<400> SEQUENCE: 2
ccagtggtac ggccagagg                                                    19

<210> SEQ ID NO 3
<211> LENGTH: 18
<212> TYPE: DNA
<213> ORGANISM: Artificial Sequence
<220> FEATURE:
<223> OTHER INFORMATION: BRN3A forward primer

<400> SEQUENCE: 3
ctacacgcac gaactgag                                                     18
```

<210> SEQ ID NO 4
<211> LENGTH: 18
<212> TYPE: DNA
<213> ORGANISM: Artificial Sequence
<220> FEATURE:
<223> OTHER INFORMATION: BRN3A reverse primer

<400> SEQUENCE: 4
aacacgcaga cagaacaa                                            18

<210> SEQ ID NO 5
<211> LENGTH: 24
<212> TYPE: DNA
<213> ORGANISM: Artificial Sequence
<220> FEATURE:
<223> OTHER INFORMATION: BRN3B forward primer

<400> SEQUENCE: 5
agcgctctca cttaccctta caca                                     24

<210> SEQ ID NO 6
<211> LENGTH: 24
<212> TYPE: DNA
<213> ORGANISM: Artificial Sequence
<220> FEATURE:
<223> OTHER INFORMATION: BRN3B reverse primer

<400> SEQUENCE: 6
aaatggtgca tcggtcatgc ttcc                                     24

<210> SEQ ID NO 7
<211> LENGTH: 21
<212> TYPE: DNA
<213> ORGANISM: Artificial Sequence
<220> FEATURE:
<223> OTHER INFORMATION: ISL-1 forward primer

<400> SEQUENCE: 7
ggttgcggca atcagattca c                                        21

<210> SEQ ID NO 8
<211> LENGTH: 21
<212> TYPE: DNA
<213> ORGANISM: Artificial Sequence
<220> FEATURE:
<223> OTHER INFORMATION: ISL-1 reverse primer

<400> SEQUENCE: 8
ttggcgcatt tgatcccgta c                                        21

<210> SEQ ID NO 9
<211> LENGTH: 20
<212> TYPE: DNA
<213> ORGANISM: Artificial Sequence
<220> FEATURE:
<223> OTHER INFORMATION: LHX2 forward primer

<400> SEQUENCE: 9
gcaccaccag cttcggacca                                          20

<210> SEQ ID NO 10
<211> LENGTH: 20
<212> TYPE: DNA
<213> ORGANISM: Artificial Sequence
<220> FEATURE:
<223> OTHER INFORMATION: LHX2 reverse primer

```
<400> SEQUENCE: 10
accagacctg gaggacccgc                                          20

<210> SEQ ID NO 11
<211> LENGTH: 20
<212> TYPE: DNA
<213> ORGANISM: Artificial Sequence
<220> FEATURE:
<223> OTHER INFORMATION: MATH5 forward primer

<400> SEQUENCE: 11
agtggggcca ggataaaaag                                          20

<210> SEQ ID NO 12
<211> LENGTH: 19
<212> TYPE: DNA
<213> ORGANISM: Artificial Sequence
<220> FEATURE:
<223> OTHER INFORMATION: MATH5 reverse primer

<400> SEQUENCE: 12
ggaacgggag gtagtggtc                                           19

<210> SEQ ID NO 13
<211> LENGTH: 20
<212> TYPE: DNA
<213> ORGANISM: Artificial Sequence
<220> FEATURE:
<223> OTHER INFORMATION: PAX6 forward primer

<400> SEQUENCE: 13
tgtccaacgg atgtgtgagt                                          20

<210> SEQ ID NO 14
<211> LENGTH: 20
<212> TYPE: DNA
<213> ORGANISM: Artificial Sequence
<220> FEATURE:
<223> OTHER INFORMATION: PAX6 reverse primer

<400> SEQUENCE: 14
tttcccaagc aaagatggac                                          20

<210> SEQ ID NO 15
<211> LENGTH: 21
<212> TYPE: DNA
<213> ORGANISM: Artificial Sequence
<220> FEATURE:
<223> OTHER INFORMATION: RAX forward primer

<400> SEQUENCE: 15
tttcaccacg taccagctgc a                                        21

<210> SEQ ID NO 16
<211> LENGTH: 21
<212> TYPE: DNA
<213> ORGANISM: Artificial Sequence
<220> FEATURE:
<223> OTHER INFORMATION: RAX reverse primer

<400> SEQUENCE: 16
tcatggagga cacttccagc t                                        21

<210> SEQ ID NO 17
```

```
<211> LENGTH: 20
<212> TYPE: DNA
<213> ORGANISM: Artificial Sequence
<220> FEATURE:
<223> OTHER INFORMATION: SIX3 forward primer

<400> SEQUENCE: 17
cggagcctgt tgcgggagtg                                              20

<210> SEQ ID NO 18
<211> LENGTH: 20
<212> TYPE: DNA
<213> ORGANISM: Artificial Sequence
<220> FEATURE:
<223> OTHER INFORMATION: SIX3 reverse primer

<400> SEQUENCE: 18
atgccgctcg gtccaatggc                                              20

<210> SEQ ID NO 19
<211> LENGTH: 20
<212> TYPE: DNA
<213> ORGANISM: Artificial Sequence
<220> FEATURE:
<223> OTHER INFORMATION: SIX6 forward primer

<400> SEQUENCE: 19
acccctacgc aggtgggcaa                                              20

<210> SEQ ID NO 20
<211> LENGTH: 20
<212> TYPE: DNA
<213> ORGANISM: Artificial Sequence
<220> FEATURE:
<223> OTHER INFORMATION: SIX6 reverse primer

<400> SEQUENCE: 20
tgaagtggcc gccttgctgg                                              20
```